(12) United States Patent
Goetz

(10) Patent No.: US 8,364,272 B2
(45) Date of Patent: Jan. 29, 2013

(54) BRAIN STIMULATION PROGRAMMING

(75) Inventor: Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 144 days.

(21) Appl. No.: 12/771,880

(22) Filed: Apr. 30, 2010

(65) Prior Publication Data

US 2011/0270348 A1    Nov. 3, 2011

(51) Int. Cl.
*A61N 1/00* (2006.01)

(52) U.S. Cl. ............... 607/45; 607/30; 607/46; 607/59; 607/62; 128/920; 128/922; 128/923

(58) Field of Classification Search ............ 607/30, 607/45, 46, 59, 62; 128/920, 922, 923
See application file for complete search history.

(56) References Cited

U.S. PATENT DOCUMENTS

| | | | |
|---|---|---|---|
| 5,713,937 A * | 2/1998 | Nappholz et al. | 607/30 |
| 7,346,382 B2 | 3/2008 | McIntyre et al. | |
| 7,366,572 B2 * | 4/2008 | Heruth et al. | 607/48 |
| 2004/0034394 A1 * | 2/2004 | Woods et al. | 607/46 |
| 2006/0217781 A1 | 9/2006 | John | |
| 2007/0043401 A1 | 2/2007 | John | |
| 2007/0083104 A1 | 4/2007 | Butson et al. | |
| 2007/0179558 A1 | 8/2007 | Gliner et al. | |
| 2007/0203546 A1 | 8/2007 | Stone et al. | |
| 2007/0288064 A1 | 12/2007 | Butson et al. | |
| 2008/0027514 A1 * | 1/2008 | DeMulling et al. | 607/60 |
| 2008/0306567 A1 * | 12/2008 | Park et al. | 607/27 |
| 2009/0118635 A1 | 5/2009 | Lujan et al. | |
| 2009/0287467 A1 | 11/2009 | Sparks et al. | |

FOREIGN PATENT DOCUMENTS

WO   WO 2006/017053 A1   2/2006

OTHER PUBLICATIONS

Modolo et al., "Impact of Cortical Input on Subthalamic Activity During Deep Brain Stimulation," Laboratoire Integration du Marteriau au Systeme, UMR CNRS 5218, Universite Bordeaux 1, Talence, France, 2008, 4 pgs.
International Search Report and Written Opinion dated Aug. 22, 2011 for Application No. PCT/US2011/028499 (10 pgs.).

\* cited by examiner

*Primary Examiner* — Niketa Patel
*Assistant Examiner* — William Levicky
(74) *Attorney, Agent, or Firm* — Shumaker & Sieffert, P.A.

(57) ABSTRACT

A programming system allows a user to program therapy parameter values for therapy delivered by a medical device by specifying a desired therapeutic outcome. In an example, the programming system presents a model of a brain network associated with a patient condition to the user. The model may be a graphical representation of a network of anatomical structures of the brain associated with the patient condition and may indicate the functional relationship between the anatomical structures. Using the model, the user may define a desired therapeutic outcome associated with the condition, and adjust excitatory and/or inhibitory effects of the stimulation on the anatomical structures. The system may determine therapy parameter values for therapy delivered to the patient based on the user input.

34 Claims, 7 Drawing Sheets

BRAIN STIMULATION PROGRAMMING

TECHNICAL FIELD

The disclosure relates to medical devices, and, more particularly, programming therapy delivered by medical devices.

BACKGROUND

Medical devices, such as electrical stimulators, may be used in different therapeutic applications. Medical electrical stimulation devices, for example, may deliver electrical stimulation therapy to a patient via implanted or external electrodes to manage a patient condition. Electrical stimulation therapy may include stimulation of nerve, muscle, or brain tissue, or other tissue within a patient. An electrical stimulation system may be fully implanted within the patient. For example, an electrical stimulation system may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

A clinician can select values for a number of programmable stimulation parameters in order to define the electrical stimulation therapy to be delivered to a patient. For example, the clinician may select a current or voltage amplitude of the stimulation, and various characteristics of the stimulation waveform. If the stimulation is delivered in the form of pulses, for example, the clinician may specify a pulse width and pulse rate. In addition, the clinician may specify an electrode configuration used to deliver stimulation, including selected electrode combinations and electrode polarities. A set of parameter values may be referred to as a stimulation program or a therapy program. A program group may include multiple programs. In some cases, therapy can be delivered according to multiple programs in a program group on a simultaneous, time-interleaved, or overlapping basis.

SUMMARY

In general, the disclosure is directed to programming stimulation that is delivered to a brain of a patient. A medical device programmer may present to a user, via a user interface, a model of a brain network associated with a patient condition. The model of the brain network may be a graphical representation of brain anatomical structures associated with the patient condition and may indicate the functional relationship between the anatomical structures. The user may provide input to specify a desired effect of therapy using the presented model, where the effect of the therapy may include a therapeutic outcome. The therapeutic outcome can include the desired efficacious therapeutic results and/or stimulation-induced side effects. For example, the user may provide input to adjust effects of the stimulation on the anatomical structures (e.g., excitatory and/or inhibitory effects on structure, or synchronization and/or desynchronization of two or more structures), or an activity in one structure that affects at least one other structure. The programmer may determine the stimulation parameter values for therapy delivered to the patient via an implantable medical device (IMD) based on the therapeutic outcome indicated by the user via the user input. In some examples, the programmer may communicate the selected stimulation parameter values to the IMD for application to the patient.

In one example, the disclosure is directed to a method comprising displaying, on a user interface of a computing device, a graphical representation of a network of interconnected anatomical structures of a patient, wherein the network includes graphical links indicating functional relationships between the anatomical structures, receiving user input via the user interface specifying at least one effect of therapy delivered by an implantable medical device to at least one of the anatomical structures of the patient, and determining, with a processor, one or more therapy parameter values with which the implantable medical device generates therapy based on the user input and the functional relationships between the anatomical structures.

In another example, the disclosure is directed to a system comprising a user interface that displays a graphical representation of a network of interconnected anatomical structures of a patient, wherein the network includes graphical links indicating functional relationships between the anatomical structures, wherein the user interface receives user input specifying at least one effect of therapy delivered by an implantable medical device to at least one of the anatomical structures of the patient, and a processor that determines one or more therapy parameter values with which the implantable medical device generates therapy based on the user input and the functional relationships between the anatomical structures.

In another example, the disclosure is directed to a system comprising means for displaying, on a user interface of a computing device, a graphical representation of a network of interconnected anatomical structures of a patient, wherein the network includes graphical links indicating functional relationships between the anatomical structures, means for receiving user input via the user interface specifying at least one effect of therapy delivered by an implantable medical device to at least one of the anatomical structures of the patient, and means for determining, with a processor, one or more therapy parameter values with which the implantable medical device generates therapy based on the user input and the functional relationships between the anatomical structures.

In another example, the disclosure is directed to an article of manufacture comprising a computer-readable medium comprising instructions that, upon execution, cause a processor to display, on a user interface of a computing device, a graphical representation of a network of interconnected anatomical structures of a patient, wherein the network includes graphical links indicating functional relationships between the anatomical structures, receive user input via the user interface specifying at least one effect of therapy delivered by an implantable medical device to at least one of the anatomical structures of the patient, and determine, with a processor, one or more therapy parameter values with which the implantable medical device generates therapy based on the user input and the functional relationships between the anatomical structures.

In another aspect, the disclosure is directed to an article of manufacture comprising a computer-readable storage medium. The computer-readable storage medium comprises computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
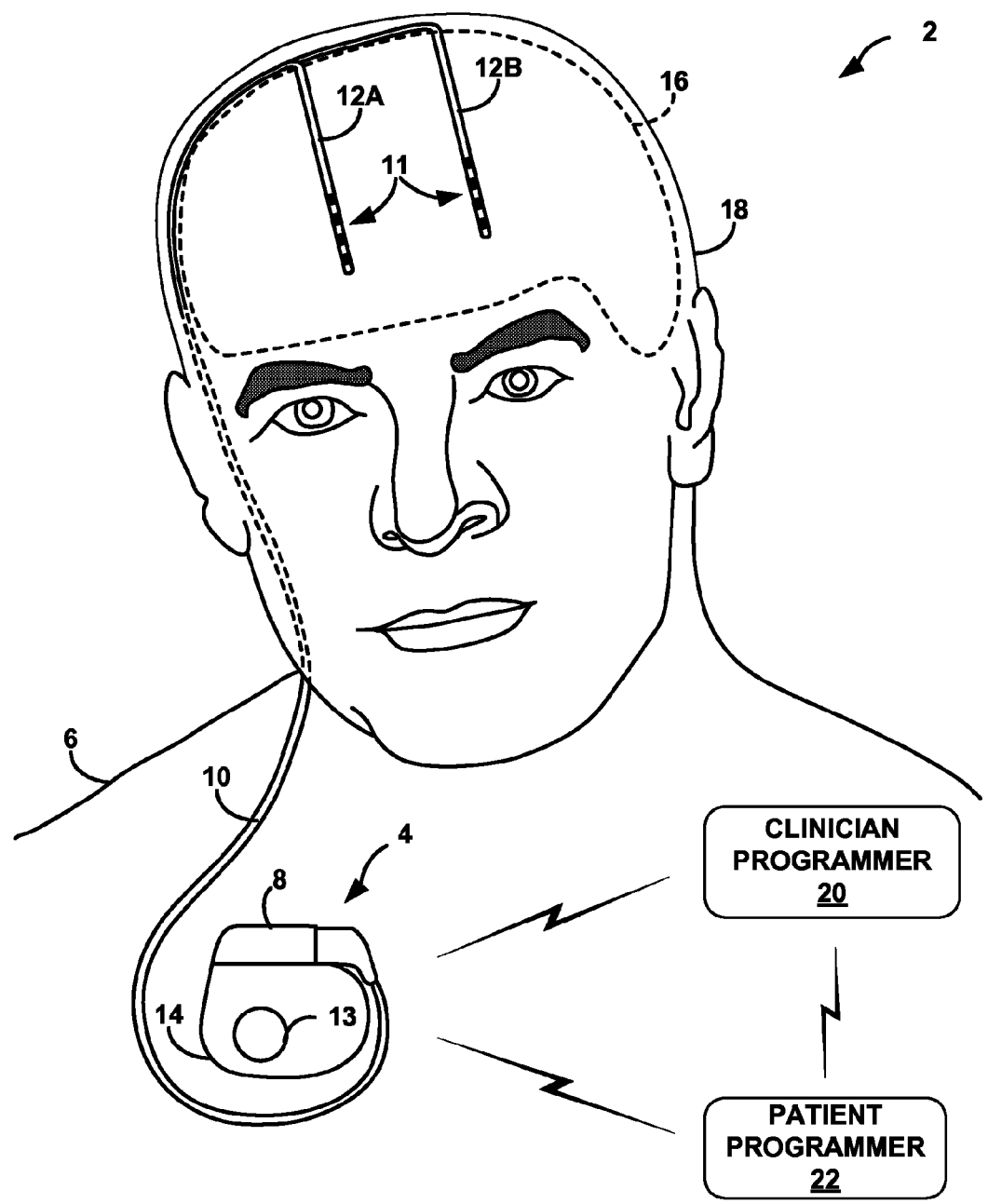
FIG. 1 is a conceptual diagram illustrating an example therapy system that includes an implantable stimulator coupled to a stimulation lead.

A therapy system, such as an electrical stimulation system, delivers therapy to a target tissue site in a patient in accordance with one or more therapy programs, where each therapy program defines one or more therapy parameter values. The therapy parameter values can be selected based on various factors, such as the type of therapy delivery member (e.g., a lead comprising electrodes, a catheter comprising a fluid delivery port, or a leadless stimulator that does not include a separate therapy delivery member), medical device or other hardware included in the therapy system, the target tissue site for the therapy delivery, the proximity of the therapy delivery member to the target tissue site, and the like. In some examples, therapy parameter values can be selected (e.g., initially selected or, if the parameter values have already been selected, modified) after implantation of the therapy delivery member in a patient. In some cases, it may be useful to modify therapy parameter values after implantation of the therapy delivery member in the patient because the actual implant site of the therapy delivery member within the patient may not correspond exactly to the intended implant location or the therapy delivery member has shifted or migrated from its implant location. Thus, if therapy parameter values are selected prior to implantation of the therapy delivery member in the patient, the selected therapy parameter values may not provide the expected therapeutic effects because, for example, the therapy delivery member is implanted at a different tissue site.

In addition, in some cases, for a given patient condition state, it can be relatively difficult to predetermine useful therapy parameter values prior to implantation of the therapy delivery member in the patient. Further, if therapy parameter values are preselected for a patient based on patient non-specific physiological information (e.g., reference anatomical image or an anatomical atlas not specific to the patient), modification to the therapy parameter values may be desirable after implantation of the therapy delivery member in the patient because the actual anatomical structures of the patient may differ in size, location, or another characteristic relative to the patient non-specific data.

In some programming systems, a user (e.g., a clinician) doctor who programs the implanted medical device (IMD) that delivers stimulation to the target region can modify the stimulation therapy by manipulating single variables, such as values of one or more stimulation parameters. Some stimulation parameters that can be adjusted include electrode configuration, current or voltage amplitude, and, in the case of stimulation pulses, pulse rate and pulse width. The user can adjust values for one or more stimulation parameter values at a time in a trial and error manner until a desired therapeutic outcome is achieved.

Due to the complexity of some therapy systems, modifying therapy by adjusting one or more individual therapy parameter values at a time can be relatively burdensome and time consuming. In addition, the complexity of some therapy systems can result in relatively long programming sessions, burdening the patient, and possibly affecting therapeutic efficacy if effective stimulation parameters are not achieved. For example, some therapy systems deliver therapy according to two or more interleaved therapy programs and/or have the ability to deliver simultaneous pulses of differing amplitudes (e.g., current steering) to target several conditions and target anatomical structures. Delivering therapy according to multiple therapy programs (e.g., parameter sets) introduces additional programming considerations that may work synergistically to achieve a desired therapeutic outcome, which the clinician may have difficulty fully understanding or appreciating.

In addition, some therapy systems include sophisticated electrode designs, such as complex electrode geometries with axially-segmented contacts, and the ability to sense local field potentials and the power spectra of sensed physiological signals at different electrode locations. Some therapy systems also include the ability to implant electrodes in distinct structures of the brain and stimulate the structures substantially simultaneously. This can be achieved using leads with non-uniformly spaced electrodes or by systems that support multiple leads, each with a set of connected or independently activatable electrodes. For example, an example therapy system may support four leads such that the system can simultaneously stimulate both the subthalamic nucleus (STN) and the external/internal globus pallidus (GPe/GPi) of a given hemisphere of the brain. Selecting stimulation parameter values for the more electrode designs (e.g., an electrode configuration more complex than a simple linear array of electrodes) or the therapy systems that deliver stimulation to multiple anatomical structures of the brain substantially simultaneously may be relatively difficult due to the synergy that may result from the different therapy parameters and other considerations.

In one method of selecting stimulation therapy parameter values, a user selects one or more stimulation parameter values based on a prediction of the volume of tissue activated by a given stimulation configuration for a specific patient's anatomy. This method abstracts the programming issues, and allows the user to better visualize the impact of parameter changes, which can help expedite the therapy parameter selection. Additionally, this method may allow the user to directly select and manipulate the volume of tissue activation. However, this method of parameter selection may not utilize an exact relationship between the volume of tissue activated and the desired therapeutic outcome in the patient. For example, in cases in which stimulation may either excite or inhibit activity in the tissue, depending on the specific stimulation parameters used (e.g., stimulation rates, implant locations of electrodes), the volume of activation is useful in making the process more efficient, but it may not be sufficient to avoid the issue of optimization of parameters, one at a time. Activity can include, for example, electrical activity or hemodynamic activity.

Devices, systems, and techniques described herein are directed to programming a medical device based on user input that specifies at least one effect of therapy delivered by a medical device to one or more anatomical structures in a brain of a patient. The effect of therapy can indicate, for example, an outcome associated with stimulating at least one structure of the brain. The user input may, for example, manipulate the activity of anatomical structures of a brain network. The anatomical structures of the brain network may be functionally related to one another via neurological pathways in a manner that causes activity within one anatomical structure of the network to be influenced by activity within another anatomical structure of the network. Aspects of the devices, systems, and techniques described herein may decrease the burden on the user in selecting stimulation therapy parameter values for a patient compared to some conventional programming techniques, and may improve efficacy of therapy for a given lead location and a given patient anatomy.

In examples described herein, a user selects one or more stimulation therapy parameter values by specifying the desired therapeutic effect of the therapy via a user interface that graphically depicts the interaction of anatomical structures of the brain. In an example, a medical device programmer presents a model of a brain network associated with a patient condition to the user. The model may resemble a network diagram, and can graphically depict representations of brain anatomical structures that are functionally connected, such that stimulation of one part of the brain network in one anatomical structure may generate excitatory and/or inhibitory effects on other anatomical structures within the brain network. For example, stimulation of one brain structure may have an excitatory effect on another structure, or cause the activity (e.g., electrical activity or hemodynamic activity) in the other brain structure to increase. In another example, stimulation of one brain structure may have an inhibitory effect on another structure, or cause the activity (e.g., electrical activity or hemodynamic activity) in the other brain structure to decrease. The model of the brain network may include graphical links between the graphical representations of the anatomical structures, where the graphical links visually indicate a functional relationship between the anatomical structures. In some examples, stimulation of one or more brain anatomical structure may result in synchronization or desynchronization between two or more brain structures. Two structures may be considered to be synchronized if their activity (e.g., electrical activity or hemodynamic activity) is correlated, or the peaks in a given spectral band of a bioelectrical brain signal representing their behaviors are relatively highly correlated (e.g., peaks of a spectral band of two brain structures occur at approximately the same time or with a consistent leading or lagging phase behavior). Two structures may be considered to be desynchronized if their activity is not correlated, or the peaks in a given spectral band representing their behavior are not correlated (e.g., the activity in one structure is not predictable given the activity in another structure). In some examples, synchronization of two or more structures may be desirable. In other examples, desynchronization of two or more structures may be desirable. For example, in epilepsy, synchronization of normally desynchronized brain structures may indicate the presence of, or predict a condition or symptom associated with epilepsy (e.g., a seizure). In this example, stimulation may be delivered to one or more of the brain structures to help desynchronize the activity of the two brain structures, therefore, mitigating or even preventing the seizure.

Using the model, the user may define a desired therapeutic outcome or adjustment to characteristics (e.g., tremor for patients with Parkinson's disease) associated with the patient condition by adjusting activity in one or more anatomical structure of the brain network represented by the model by interacting with the user interface. The programmer can then determine stimulation therapy parameter values that may achieve the desired therapeutic effect of the stimulation therapy. In some examples, the programmer may store the selected stimulation therapy parameter values and/or may communicate the parameter values to the IMD for stimulation therapy delivery.

The examples of this disclosure discuss utilizing a stimulator with leads, for illustration. Aspects of this disclosure may be applicable to leadless stimulators and other types of medical devices capable of providing stimulation therapy.

FIG. 1 is a conceptual diagram illustrating an example therapy system 2 including an implantable electrical stimulator 34 that delivers stimulation therapy to patient 6. Patient 6 ordinarily, but not necessarily, will be a human. In the example shown in FIG. 1, therapy system 2 may be referred to as a deep brain stimulation (DBS) system because implantable electrical stimulator 4 delivers electrical stimulation therapy directly to tissue within brain 16, such as under the dura matter of brain 16. In addition to or instead of deep brain sites, implantable electrical stimulator 4 may deliver electrical stimulation to target tissue sites on a surface of brain 16, such as between the patient's cranium and the dura mater of brain 16 (e.g., the cortical surface of brain 16). Implantable stimulator 4 can deliver therapy to brain 16 of patient 6 to treat any of a variety of patient conditions, such as neurological disorders or diseases. Example neurological disorders may include depression, dementia, obsessive-compulsive disorder, and movement disorders, such as Parkinson's disease, spasticity, epilepsy, and dystonia. DBS may also be useful for treating other patient conditions, such as migraines, obesity, and mood disorders (e.g., depression or an anxiety disorder).

Implantable electrical stimulator 4 delivers electrical stimulation to patient 6 via one or more implantable electrodes 11. The implantable electrodes 11 may be deployed on one or more implantable medical leads, such as implantable medical lead 10 with lead segments 12A and 12B, and, in some cases, on a housing 14 of the medical device. The electrical stimulation may be in the form of controlled current or voltage pulses or substantially continuous waveforms. Various parameters of the pulses or waveforms may be defined by one or more therapy programs (also referred to as "stimulation programs" in the case of stimulation therapy). The pulses or waveforms may be delivered substantially continuously or in bursts, segments, or patterns, and may be delivered alone or in combination with pulses or waveforms defined by one or more other stimulation programs. Although FIG. 1 shows a fully implantable stimulator 4, techniques described in this disclosure may be applied to external stimulators having electrodes deployed via percutaneously implantable leads with a patch electrode or other indifferent electrode attached externally to serve as the reference electrode. In addition, in some cases, implantable electrodes may be deployed on a leadless stimulator, in which case stimulator 4 may not be coupled to lead 10.

In the example illustrated in FIG. 1, implantable stimulator 4 is implanted within a subcutaneous pocket in a clavicle region of patient 6. Stimulator 4 generates programmable electrical stimulation, e.g., a current or voltage waveform, or current or voltage pulses, and delivers the stimulation via an implantable medical lead 10 carrying an array of implantable stimulation electrodes 11. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, twelve, sixteen, or more electrodes, although system 2 can include any suitable number of electrodes on any suitable number of leads. In the example shown in FIG. 1, each lead segment 12A, 12B includes four electrodes, which are configured as ring electrodes at different axial positions near the distal ends of the lead segments. Throughout the remainder of this disclosure, for purposes of simplicity, the disclosure may generally refer to electrodes carried on "leads" rather than "lead segments."

FIG. 1 further depicts a housing, or can, electrode 13. Housing electrode 13 may be formed integrally with an outer surface of hermetically-sealed housing 14 of implantable stimulator 4 (also referred to in this disclosure as implantable medical device (IMD) 4), or otherwise coupled to housing 14. In one example, housing electrode 13 may be described as an active, non-detachable electrode on the surface of the IMD. In some examples, housing electrode 13 is defined by an uninsulated portion of an outward facing portion of housing 14 of IMD 4. Other divisions between insulated and uninsulated portions of housing 14 may be employed to define two or more housing electrodes, which may be referred to as case or can electrodes. In some examples, housing electrode 13 comprises substantially all of housing 14, one side of housing 14, a portion of the housing 14, or multiple portions of housing 14. In other examples, electrode 13 may be formed by an electrode on a dedicated short lead extending from housing 14. As a further alternative, housing electrode 13 could be provided on a proximal portion of one of the leads carrying electrodes 11. The proximal portion may be closely adjacent to housing 14, e.g., at or near a point at which lead 10 is coupled to the housing, such as adjacent to a lead connection header 8 of the housing. In another example, a patch electrode or other indifferent electrode may be attached externally to serve as the reference electrode.

In some examples, lead 10 may also carry one or more sense electrodes to permit implantable stimulator 4 to sense electrical signals from patient 6. Some of the stimulation electrodes may be coupled to function as stimulation electrodes and sense electrodes on a selective basis. In other examples, implantable stimulator 4 may be coupled to one or more leads which may or may not be bifurcated. In such examples, the leads may be coupled to implantable stimulator 4 via a common lead extension or via separate lead extensions.

A proximal end of lead 10 may be both electrically and mechanically coupled to header 8 on implantable stimulator 4, either directly or indirectly via a lead extension. Conductors in the lead body of lead 10 may electrically connect stimulation electrodes located on lead segments 12 to implantable stimulator 4. Lead 10 traverses from the implant region of implantable stimulator 4 along the neck of patient 6 to cranium 18 of patient 6 to access brain 16. Lead segments 12A and 12B are implanted within the right and left hemispheres, respectively, in order to deliver electrical stimulation to one or more structures of brain 16, which may be selected based on the patient condition. The disclosure is not limited to the configuration of lead 10 shown in FIG. 1, or to the delivery of DBS or CS therapy.

Lead segments 12A, 12B may be implanted within a desired location of brain 16 through respective holes in cranium 18. Lead segments 12A, 12B may be placed at any location within brain 16 such that the electrodes 11 located on lead segments 12A, 12B are capable of providing electrical stimulation to a target therapy delivery site within brain 16. In the case of movement disorders, example locations for lead segments 12A, 12B within brain 16 may include the pedunculopontine nucleus (PPN), thalamus, basal ganglia structures (e.g., globus pallidus, substantia nigra, subthalamic nucleus), zona inserta, fiber tracts, lenticular fasciculus (and branches thereof), ansa lenticularis, and/or the Field of Forel (thalamic fasciculus). In the case of migraines, lead segments 12 may be implanted to provide stimulation to the visual cortex of brain 16 in order to reduce or eliminate migraine headaches afflicting patient 6. In general, the target therapy delivery site may depend upon the patient condition being treated.

In the example shown in FIG. 1, electrodes 11 of lead segments 12 are ring electrodes. Ring electrodes are relatively simple to program and are capable of delivering an electrical field to any tissue adjacent to lead segments 12. In other examples, electrodes 11 of lead segments 12 may have different configurations. For example, electrodes 11 of lead segments 12 may have a complex electrode array geometry that is capable of producing shaped electrical fields. The complex electrode array geometry may include multiple electrodes (e.g., partial ring or segmented electrodes) around the outer perimeter of each lead segment 12A, 12B, rather than one ring electrode. In this manner, electrical stimulation may be directed in a specific direction from lead segments 12 to enhance therapy efficacy and reduce possible adverse side effects from stimulating a large volume of tissue. In alternative examples, one or both lead segments 12 may have shapes other than elongated cylinders as shown in FIG. 1. For example, lead segments 12 may be paddle leads, spherical leads, bendable leads, or any other type of shape effective in treating patient 6.

In the example shown in FIG. 1, therapy system 2 includes clinician programmer 20 and patient programmer 22. Clinician programmer 20 may be a computing device that permits a clinician to program stimulation therapy delivered by stimulator 4 via a user interface, e.g., using input keys and a display. For example, using clinician programmer 20, the clinician may specify stimulation parameter values, i.e., create therapy programs, for use in delivery of stimulation therapy by stimulator 4. Clinician programmer 20 may support telemetry (e.g., radio frequency (RF) telemetry) with implantable stimulator 4 to download programs and, optionally, upload operational or physiological data stored by implantable stimulator 4. In this manner, the clinician may periodically interrogate implantable stimulator 4 with clinician programmer 20 to evaluate efficacy based on the stored physiological data and, if necessary, modify the programs or create new programs. In some examples, clinician programmer 20 transmits programs to patient programmer 22 in addition to or instead of implantable stimulator 4.

In some examples, patient programmer 22 may serve as the clinician programmer. In some examples, a programmer can be a dedicated computing device or it can be any suitable general purpose computing device that can be used for programming purposes. In other examples, a programmer may be a device that serves as a client device to a workstation or server infrastructure connected via a network, where the workstation or server supplies computational capability (e.g., to determine one or more therapy parameter values based on user input indicating a desired therapeutic effect of stimulation therapy), communicates results to the programmer, and the programmer displays the results at a point of use.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop or adjust electrical stimulation therapy. In particular, patient programmer 22 may permit patient 6 to adjust stimulation parameters of a program such as duration, current or voltage amplitude, pulse width and pulse rate. Patient 6 may also select a therapy program, e.g., from among a plurality of stored therapy programs, as the present program to control delivery of stimulation by implantable stimulator 4. In one example, patient programmer 22 may have permissions associated with the therapy programs it controls, and may give patient 6 the ability to change certain parameter values and/or programs.

A user can interact with clinician programmer 20, patient programmer 22 or another computing device to define stimulation therapy parameter values for generation by stimulator 4 and delivery to a target tissue site within brain 16 of patient 12 by one or more leads 10. While the disclosure primarily refers to a user interface presented by clinician programmer 20 for programming stimulation therapy delivered by stimulator 4, in other examples, the techniques described herein can be performed by patient programmer 22 or another computing device. Thus, the description of clinician programmer 20 can also be relevant to patient programmer 22 or another computing device.

In some examples described herein, clinician programmer 20 generates and displays a graphical user interface that presents a high level model of a brain network that includes functionally related anatomical structures of the brain associated with a patient condition, where stimulation applied to one anatomical structure of the network affects one or more other anatomical structures of the network and the characteristics associated with the patient condition (e.g., one or more symptoms, presence/absence/severity of side effects such as paresthesias, blurred vision, cognitive deficits, and the like). The user can select at least one effect of therapy delivered by stimulator 4 to one or more anatomical structures within the brain network by interacting with the user interface. The effect of therapy may be, for example, a desired therapeutic outcome for the stimulation therapy delivered to patient 6. For example, the user can adjust activity in the one or more anatomical structure of the brain network represented by the model by interacting with the user interface. The activity may be, for example, bioelectrical brain signal activity or hemodynamic activity. Examples of bioelectrical brain signals include, but are not limited to, electrical signals generated from local field potentials (LFP) sensed within one or more structures of brain 28, such as an electroencephalogram (EEG) signal, or an electrocorticogram (ECoG) signal. LPFs, however, may include a broader genus of electrical signals within brain 28 of patient 12. Hemodynamic activity within a brain structure may be indicated by, for example, blood flow, blood pressure, or blood volume within the brain structure.

In response to receiving user input indicating a desired therapeutic outcome, clinician programmer 20 can select the stimulation parameter values that may achieve the user-selected therapeutic outcome. For example, clinician programmer 20 can translate one or more user-selected therapeutic outcomes into a subset of electrodes 11 for delivering electrical stimulation therapy to a patient and the values of the stimulation signal delivered via the subset of electrodes 11. In this way, the user can select one or more stimulation parameter values by selecting a desired therapeutic outcome via the user interface of clinician programmer 20.

In one example, clinician programmer 20 presents a model of a brain network associated with a patient condition and receives input from a user that indicates the desired effect on certain structures of the brain network, where the structures may represent respective structures of the brain. In one example, clinician programmer 20 may allow the user to utilize a user interface to change the inhibitory and/or excitatory effects on brain structures and/or to induce synchronization or desynchronization between two or more brain structures within the model of the brain network, and the stimulation therapy parameter values may be adjusted accordingly to achieve user-specified effects.

In one example, implantable stimulator 4 delivers stimulation therapy according to the stimulation therapy parameter values selected by programmer 20 based on user input. The therapy parameter values may be organized as a therapy program or as a group of therapy programs. Each therapy program may include respective values for each of a plurality of therapy parameters, such as respective values for each of current or voltage amplitude, pulse width, pulse shape, pulse rate and electrode configuration (e.g., electrode combination and polarity). In some examples, implantable stimulator 4 delivers stimulation according to a group of therapy programs at a given time. Implantable stimulator 4 may interleave pulses or other signals according to the different programs of a program group, e.g., cycle through the programs, to simultaneously treat different symptoms or different body regions, or provide a combined therapeutic effect.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art or other standard communication protocols such as, for example, Bluetooth®. Clinician programmer 20 and patient programmer 22 also may communicate with each other using any of a variety of wired or wireless communication techniques, such as RF communication according to the 802.11 or Bluetooth® specification sets, infrared communication, e.g., according to the IrDA standard, or other standard or proprietary telemetry protocols. Each of clinician programmer 20 and patient programmer 22 may include a transceiver to permit bi-directional communication with implantable stimulator 4.

Although the disclosure generally refers to implantable stimulators for purposes of illustrations, techniques described in this disclosure also may be used with other types of implantable medical devices and for conditions associated with other organs or parts of a patient's body. Accordingly, description of implantable stimulators is provided for purposes of illustration and should not be considered limiting of the techniques as broadly described in this disclosure.

Figure 2:
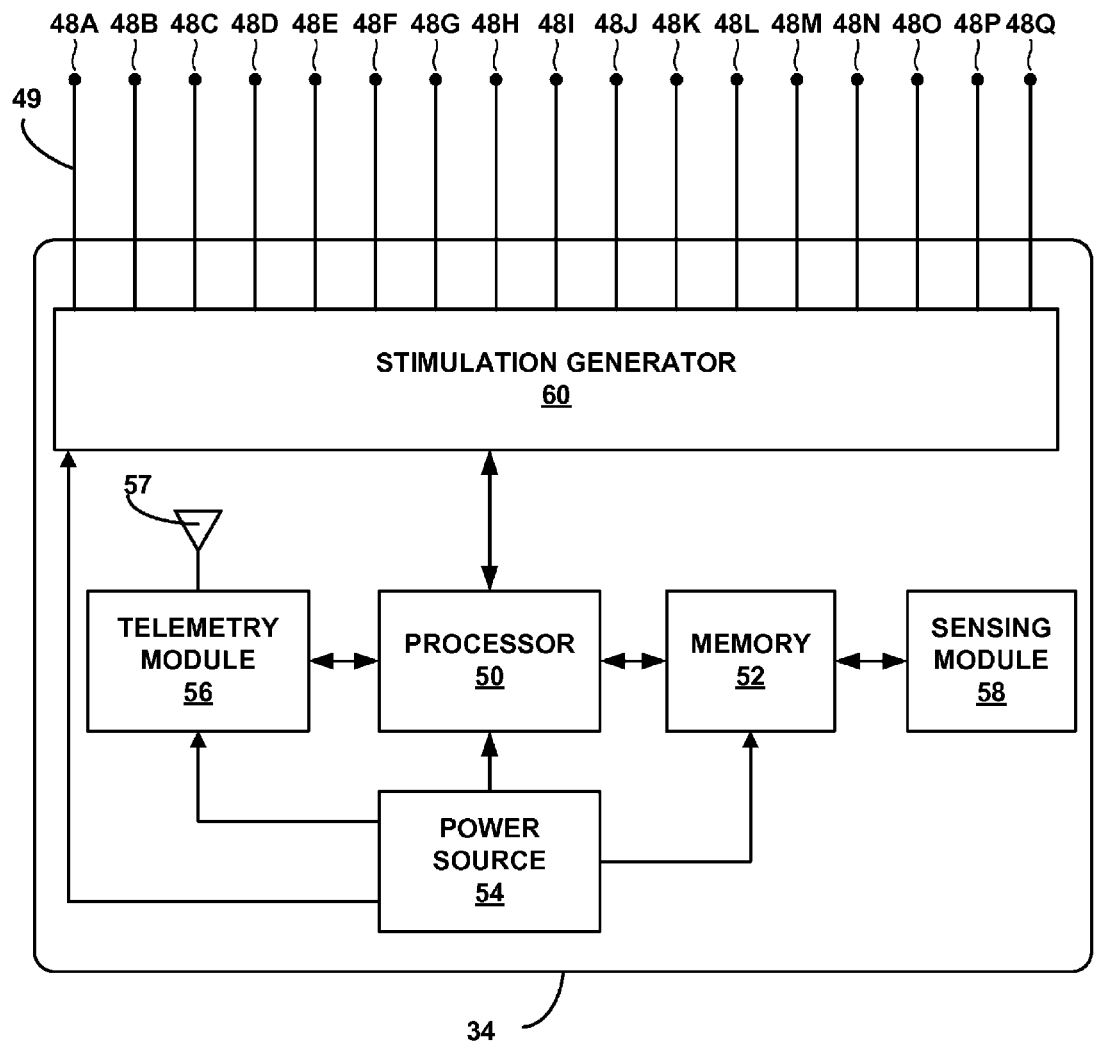
FIG. 2 is a functional block diagram illustrating example components of an example implantable electrical stimulator.

FIG. 2 is a functional block diagram illustrating various components of an example implantable stimulator 34. Implantable stimulator 34 is an example of implantable stimulator 4 shown in FIG. 1. In the example shown in FIG. 2, implantable stimulator 34 includes processor 50, memory 52, power source 54, telemetry module 56, antenna 57, sensing module 58, and stimulation generator 60. Implantable stimulator 34 is also shown in FIG. 2 coupled to each of the electrodes 48A-48Q (collectively "electrodes 48") via a respective conductor. In some examples, two or more electrodes 48 may be coupled to stimulation generator 60 via a common conductor. Electrodes 48A-48P are implantable and may be deployed on one or more implantable leads. With respect to FIG. 1, lead segments 12A and 12B may carry electrodes 48A-48H and electrodes 48I-48P, respectively. In some cases, one or more additional electrodes may be located on or within the housing of implantable stimulator 34, e.g., to provide a common or ground electrode or a housing anode. In the example of FIG. 1, a lead or lead segment carries eight electrodes to provide an 2×8 electrode configuration (e.g., two leads with 8 electrodes each or an array of electrodes comprising two columns and eight rows), providing a total of sixteen different electrodes. The leads may be detachable from a housing associated with implantable stimulator 34, or be fixed to such a housing.

In other examples, a therapy system can include different electrode configurations comprising a single lead, two leads, three leads, or more than three leads. In addition, electrode counts on leads may vary and may be the same or different from lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), or other configurations. In addition, in other examples, stimulation generator 60 may deliver stimulation to patient 6 via electrodes on a paddle lead, which can have a paddle-shaped distal end that may include multiple columns and rows of electrodes. Different electrodes are selected to form electrode combinations. Polarities are assigned to the selected electrodes to form electrode configurations.

Memory 52 may store instructions for execution by processor 50, stimulation therapy data and/or other information regarding therapy for patient 6. Processor 50 may control stimulation generator 60 to generate and deliver stimulation according to a selected one or more of a plurality of therapy programs or program groups stored in memory 52. Each stored therapy program defines a particular set of electrical stimulations parameters, such as a stimulation electrode combination or configuration, current or voltage amplitude, frequency (e.g., pulse rate in the case of stimulation pulses), and pulse width. Memory 52 may include any electronic data storage media, such as random access memory (RAM), read-only memory (ROM), electronically-erasable programmable ROM (EEPROM), flash memory, or the like. Memory 52 may store program instructions that, when executed by processor 50, cause the processor to perform various functions ascribed to processor 50 and implantable stimulator 34 in this disclosure.

In some examples, information stored by memory 52 may include information regarding therapy that patient 6 had previously received or information regarding a current therapy regimen. Storing both historical and current therapy information may be useful for subsequent therapy such that, for example, a clinician may retrieve the stored information to determine the therapy applied to the patient during a previous therapy session. The information stored in memory 52 may also include, for example, information regarding the brain structures associated with patient condition and the corresponding stimulation therapy program defined by stimulation therapy parameter values, where applying the stimulation therapy program helps control the anatomical structures of the brain to achieve a desired therapeutic outcome for the associated patient condition.

Processor 50 may include one or more microprocessors, digital signal processors (DSPs), application-specific integrated circuits (ASICs), field-programmable gate arrays (FPGAs), or other digital logic circuitry. Functions attributed to processors described herein may be embodied in a hardware device via software, firmware, hardware, or any combination thereof. Processor 50 controls operation of implantable stimulator 34, e.g., controls stimulation generator 60 to generate and deliver stimulation therapy according to a selected therapy program or group of therapy programs retrieved from memory 52. For example, processor 50 may control stimulation generator 60 to deliver electrical signals, e.g., as stimulation pulses or continuous waveforms, with current or voltage amplitudes, pulse widths (if applicable), and rates specified by one or more stimulation programs. Processor 50 may also control stimulation generator 60 to selectively deliver the stimulation via subsets of electrodes 48, also referred to as electrode combinations, and with polarities specified by one or more programs.

Upon selection of a particular program, processor 50 may control stimulation generator 60 to deliver stimulation according to the selected therapy program or programs in the groups, e.g., simultaneously or on a time-interleaved basis. A group may include a single therapy program or multiple therapy programs. As mentioned previously, each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and status of the electrodes. The electrode combination may specify particular electrodes in a single array or multiple arrays, and on a single lead or among multiple leads.

Figure 3:
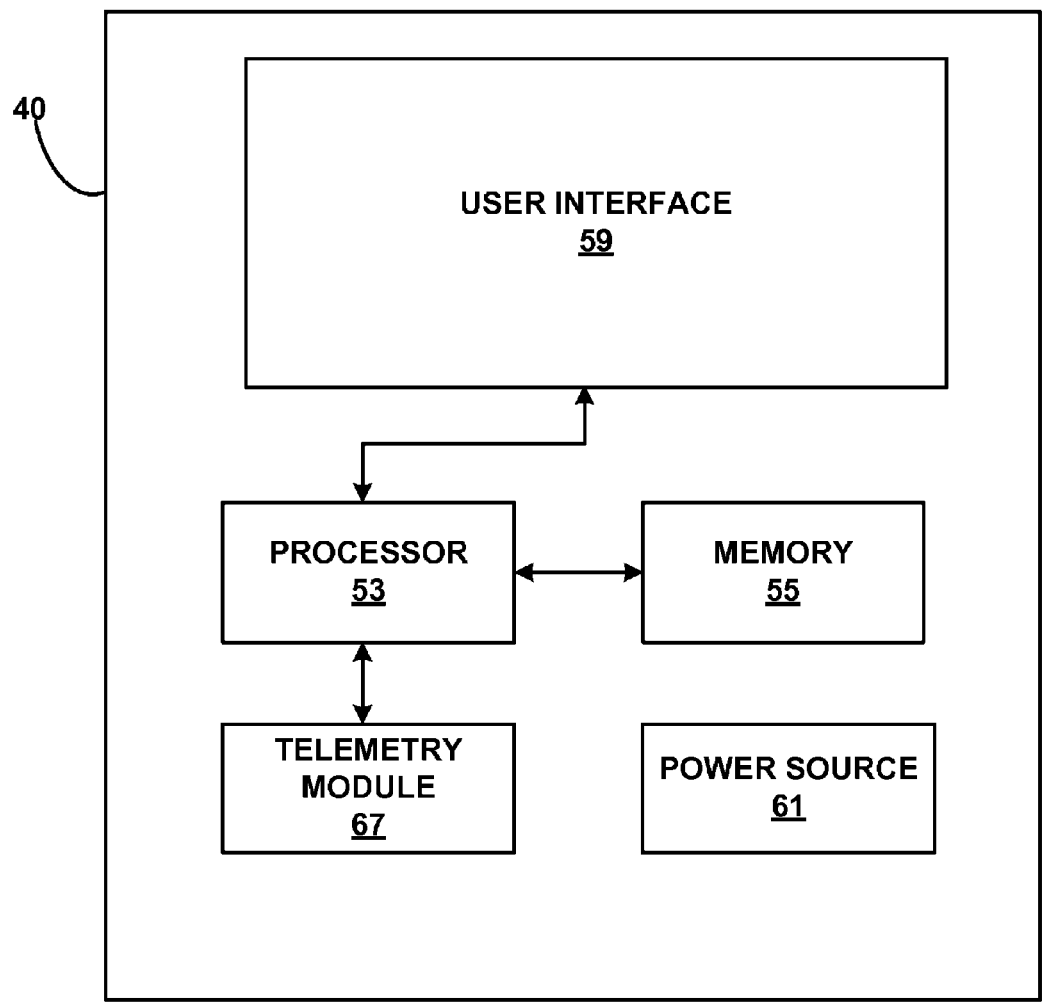
FIG. 3 is a functional block diagram illustrating example components of an example external programmer.

Stimulation generator 60 is electrically coupled to electrodes 48A-48P via conductors 49 of the respective lead, such as lead 10 in FIG. 1, in implementations in which electrodes 48A-48P are carried by (e.g., located on) leads. As described above, in some examples, electrodes 48A-48P can be carried by a common lead or by two or more separate leads. Thus, conductors 49 can be conductors of one or more leads. Stimulation generator 60 may be electrically coupled to one or more housing ("can") electrodes 48Q via an electrical conductor disposed within the housing of implantable stimulator 4 (FIG. 1) or implantable stimulator 34 (FIG. 3). A housing electrode 48Q may be configured as a regulated or unregulated electrode to form an electrode configuration in conjunction with one or more of electrodes 48A-48P located on leads coupled to stimulator 34. For example, housing electrode 48Q may be configured for use as an anode to source current substantially simultaneously with one or more electrodes, e.g., any of electrodes 48A-48P, on one or more leads configured for use as cathodes.

Stimulation generator 60 may include stimulation generation circuitry to generate stimulation pulses or waveforms and circuitry for switching stimulation across different electrode combinations, e.g., in response to control by processor 50. Stimulation generator 60 produces an electrical stimulation signal in accordance with a program based on control signals from processor 50. Stimulation generator 60 can be a single channel or multi-channel stimulation generator. For example, stimulation generator 60 may be capable of delivering a single stimulation pulse, multiple stimulation pulses, or a continuous signal at a given time via a single electrode combination or multiple stimulation pulses at a given time via multiple electrode combinations.

In some examples, stimulation generator 60 may include a charging circuit that selectively applies energy from power source 54 to a capacitor module for generation and delivery of a supply voltage for generation of stimulation signal. In addition to capacitors, the capacitor module may include switches. In this manner, the capacitor module may be configurable, e.g., based on signals from processor 50, to store a desired voltage for delivery of stimulation at a voltage or current amplitude specified by a program. For delivery of stimulation pulses, switches within the capacitor module may control the widths of the pulses based on signals from processor 50.

Sensing module 58 may be configured to sense a physiological parameter of patient 6, such as a bioelectrical brain signal within brain 16 (e.g., local field potentials (LPF) signals which include EEG and ECoG signals, or a broader genus of electrical signals within brain 16) or a hemodynamic characteristic (e.g., blood pressure, blood volume, or blood flow) within brain 16. Sensing module 58, under the control of processor 50 (or a processor of another device, such as programmer 20 of FIG. 1), may sense bioelectrical signals or another signal indicative of a patient parameter and provide the sensed signals to processor 50. To sense bioelectrical brain signals, processor 50 may control sensing module 58 to selectively sense bioelectrical brain signals with sub-combinations of electrodes 48A-48P. In this manner, stimulator 34 may be configured such that sensing module 58 may sense bioelectrical signals with different combinations of electrodes 48A-48P. Although sensing module 58 is incorporated into a common housing with stimulation generator 60 and processor 50 in the example shown in FIG. 2, in other examples, sensing module 58 may be in a physically separate housing from stimulator 34 and may communicate with processor 50 via wired or wireless communication techniques. Sensing module 58 may receive the bioelectrical signals from electrodes 48A-48P or other electrodes positioned to monitor brain signals of patient 6. Processor 50 may receive the output of sensing module 58, which may be raw bioelectrical signals. In other examples, processor 50 may apply additional processing to the bioelectrical signals, e.g., convert the signals to digital values for further processing, filter the signals, and the like. In one example, sensing module 58 may be configured to sense hemodynamic characteristics (e.g., blood pressure, blood volume, or blood flow). In this example, sensing module 58 may include circuitry such as, for example, a pressure sensor, a pulse oximeter, and the like for sensing hemodynamic characteristics.

Telemetry module 56 supports wireless communication between implantable stimulator 34 and an external programmer 20 and/or 22, or another computing device under the control of processor 45. Telemetry module 56 may include a RF transceiver to permit bi-directional communication between implantable stimulator 34 and each of clinician programmer 20 and patient programmer 22. In one example, telemetry module 56 may utilize other communication protocols and a corresponding transceiver, for example, a Bluetooth® transceiver for telemetry using the Bluetooth® protocol. Telemetry module 56 may include an antenna 57 that may take on a variety of forms. For example, antenna 57 may be formed by a conductive coil or wire embedded in a housing associated with medical device 4. Instead or in addition to the conductive coil or wire, antenna 57 may be mounted on a circuit board carrying other components of implantable stimulator 34 or take the form of a circuit trace on the circuit board. In this way, telemetry module 56 may permit communication with clinician programmer 20 and patient programmer 22 in FIG. 1, to receive, for example, new programs or program groups, or adjustments to programs or program groups.

Telemetry module 56 may also communicate information regarding previous therapy sessions that have been stored in memory 52, to an external programmer during a subsequent therapy session; the information regarding a previous therapy session may have been imported by a programmer used in the previous session. The stored information may include, for example, lead placement in the patient, stimulation therapy parameter values, desired therapy outcome defined by the user for a particular program, patient information, clinic(s) where patient had previously received treatments, previous clinician information, and the like.

Power source 54 may be a non-rechargeable primary cell battery or a rechargeable battery and may be coupled to power circuitry. However, the disclosure is not limited to examples in which the power source is a battery. In another example, as an example, power source 54 may comprise a supercapacitor. In some examples, power source 54 may be rechargeable via induction or ultrasonic energy transmission, and include an appropriate circuit for recovering transcutaneously received energy. For example, power source 54 may be coupled to a secondary coil and a rectifier circuit for inductive energy transfer. In additional examples, power source 54 may include a small rechargeable circuit and a power generation circuit to produce the operating power. Recharging may be accomplished through proximal inductive interaction between an external charger and an inductive charging coil within stimulator 34. In some examples, power requirements may be small enough to allow stimulator 34 to utilize patient motion at least in part and implement a kinetic energy-scavenging device to trickle charge a rechargeable battery. A voltage regulator may generate one or more regulated voltages using the battery power.

FIG. 3 is a functional block diagram illustrating various components of an example external programmer 40 for an implantable stimulator 34. External programmer 40 is an example of clinician programmer 20 or patient programmer 22 shown in FIG. 1. As shown in FIG. 3, external programmer 40 includes processor 53, memory 55, telemetry module 67, user interface 59, and power source 61. In general, processor 53 controls user interface 59 and receives user input via user interface 59, stores and retrieves data to and from memory 55, and controls transmission of data with implantable stimulator 34 through telemetry module 67. Processor 53 may take the form of one or more microprocessors, controllers, DSPs, ASICS, FPGAs, or equivalent discrete or integrated logic circuitry. The functions attributed to processor 53 herein may be embodied as software, firmware, hardware or any combination thereof.

Memory 55 may store instructions that cause processor 53 to provide various aspects of the functionality ascribed to external programmer 40 herein. Memory 55 may include any fixed or removable magnetic, optical, or electrical media, such as RAM, ROM, CD-ROM, magnetic disks, EEPROM, or the like. In some examples, memory 55 may also include a removable memory portion that may be used to provide memory updates or increases in memory capacities. A removable memory may also allow patient data to be easily transferred to another computing device, or to be removed before programmer 40 is used to program therapy for another patient. Memory 55 may also store information that controls operation of implantable stimulator 34, such as therapy delivery values. In some examples, memory 55 may store therapy program information, which may be transferred to the stimulator 34.

User interface 59 may include a display screen and one or more input buttons that allow external programmer 40 to receive input from a user. The screen may be, for example, a liquid crystal display (LCD), light emitting diode (LED) display, plasma display, dot matrix display, or touch screen. The input buttons may include a touch pad, increase and decrease buttons, emergency shut off button, and other input media needed to control the stimulation therapy. The input buttons may be dedicated to performing a certain function, i.e., a power button, or the buttons may be soft keys that change in function depending upon the section of the user interface presented by the display of user interface 59 currently viewed by the user.

A clinician or patient 6 interacts with user interface 59 in order to, for example, manually select, change, or modify therapy programs, e.g., by adjusting voltage or current amplitude, adjusting pulse rate, adjusting pulse width, or selecting different electrode combinations or configurations, and may provide efficacy feedback or view stimulation data via user interface 59. In some examples, user interface 59 displays a model of a brain network associated with a condition of patient 6. The model may resemble a network diagram, and can graphically depict representations of brain anatomical structures that are functionally connected, such that stimulation of one part of the brain network in one structure may generate excitatory and/or inhibitory effects on one or more other structures within the brain network. In one example, stimulation of one or more parts of the brain network may induce synchronization or desynchronization between two or more brains structures.

In one example, the effects on the brain structures are associated with the patient condition, e.g., a therapeutic outcome that includes minimizing or eliminating one or more symptoms of the patient condition. The user, e.g., a clinician, may use the input buttons (e.g., physical buttons of the user interface that can be depressed or otherwise activated by a user or buttons displayed on a touch-screen of the user interface) of user interface 59 to specify a desired therapeutic outcome of stimulation applied to the structures of the brain network represented by the model, where the therapeutic outcome can include beneficial therapeutic effects and/or stimulation-induced side effects associated with the patient condition. Processor 53 may then determine stimulation therapy parameter values that define a stimulation therapy program that may help achieve the desired therapeutic outcome indicated by the patient when stimulator 34 delivers therapy to patient 6 in accordance with the therapy program. In this manner, the user may be able to configure stimulation therapy parameter values by specifying the desired therapeutic effect for the stimulation delivered by stimulator 34.

Programmer 40 may communicate wirelessly with implantable stimulator 34 via telemetry module 67, which may include an internal antenna and/or an external antenna. Telemetry module 67 can be configured to support the transfer of data to and from stimulator 34. Telemetry module 67 may communicate automatically with stimulator 34 at a scheduled time or when the telemetry module detects the proximity of the stimulator. Alternatively, telemetry module 67 may communicate with stimulator 34 when signaled by a user through user interface 59. To support RF communication, telemetry module 44 may include appropriate electronic components, such as amplifiers, filters, mixers, encoders, decoders, and the like. In other examples, telemetry module 67 may employ other communication standards such as, for example, Bluetooth® and telemetry module 67 may include the appropriate Bluetooth® components.

Programmer 40 may communicate wirelessly with implantable stimulator 34 using, for example, RF communication or proximal inductive interaction or other communication standards such as, for example, Bluetooth®. In some examples, telemetry module 67 may be similar to telemetry module 56 (FIG. 2) of implantable stimulator 34. In accordance with this disclosure, programmer 40 may communicate stimulation parameter values determined based on a desired therapeutic outcome specified by the user to stimulator 34 via telemetry module 67. Additionally, programmer 40 may access models of a brain network associated with a patient condition and any previously-defined therapeutic outcomes for viewing and manipulation by the user via user interface 59. Programmer 40 may also retrieve information regarding placement of leads in structures associated with the brain network model that the user is currently viewing. In some examples, patient 6 may be associated with one or more patient conditions, and programmer 40 may retrieve information regarding a selected patient condition or all patient conditions.

Programmer 40 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth® specification sets, infrared communication, e.g., based on the IrDA standard.

Power source 61 delivers operating power to the components of programmer 40. Power source 61 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. Power source 61 may include circuitry to monitor power remaining within a battery. In this manner, user interface 59 may provide a current battery level indicator or low battery level indicator when the battery needs to be replaced or recharged. In some cases, power source 61 may be capable of estimating the remaining time of operation using the current battery.

A user of programmer 40 may utilize user interface 59 to select one or more stimulation parameter values for stimulation generated and delivered by stimulator 34 by indicating a desired therapeutic outcome (e.g., a balance of beneficial therapeutic effects and/or stimulation-induced side effects) for a patient condition of patient 6. In response to receiving input indicating a desired therapeutic outcome for a selected patient condition, processor 53 of programmer 40 selects one or more therapy parameter values that may achieve the desired therapeutic outcome. The one or more therapy parameter values can define a therapy program.

In some examples, user interface 59 may display a model of a brain network associated with the patient condition. In some examples, the model represents a brain network diagram that includes graphical representations corresponding to brain structures affected by excitatory and/or inhibitory stimulation, where applying stimulation to one structure in the brain network has an excitatory and/or inhibitory effect on one or more other structures in the brain network. The user may select the desired therapeutic outcome by adjusting the excitatory and/or inhibitory impact on the structures in the brain network represented by the model. Processor 53 may translate the user inputs into stimulation therapy parameter values that result in the desired therapeutic outcome when applied by stimulator 34. In this manner, the user may be able to select and configure stimulation therapy parameter values by specifying the desired therapeutic effect of brain therapy that is delivered by stimulator 34 in accordance with this disclosure.

In some examples, programmer 40 can be configured to store a plurality of different brain networks for respective patient conditions, such that processor 53 can present, via user interface 59, a plurality of patient conditions for selection by a user.

Figure 4A:
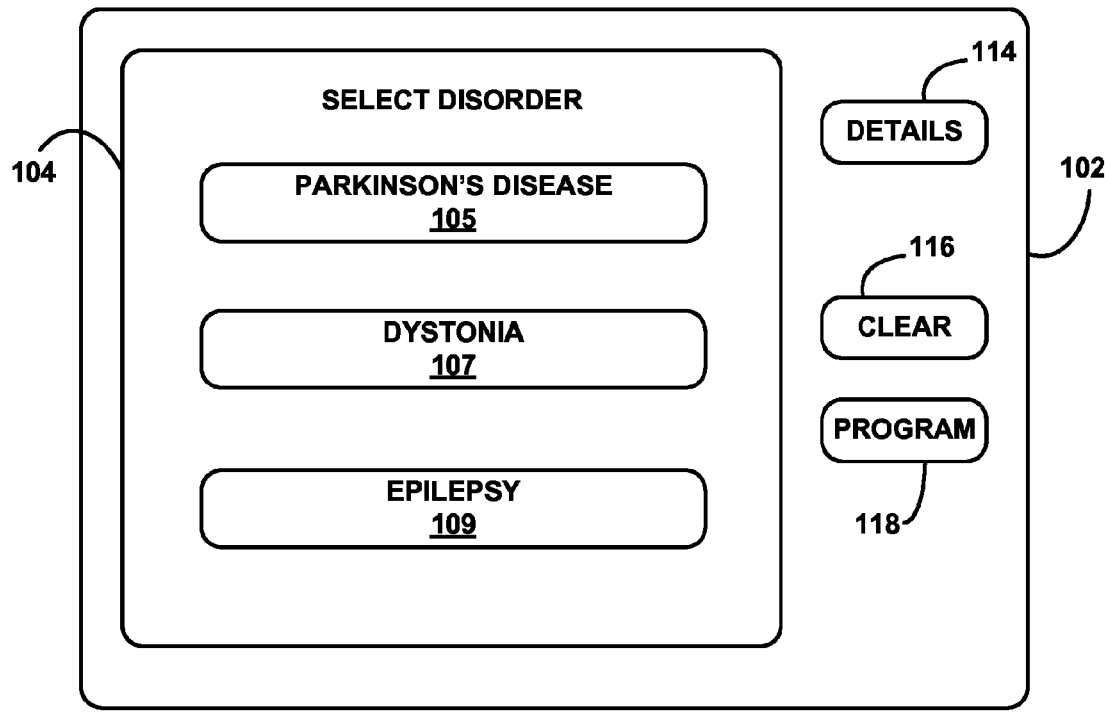
FIGS. 4A-4C illustrate example programmer user interfaces.
Figure 4B:
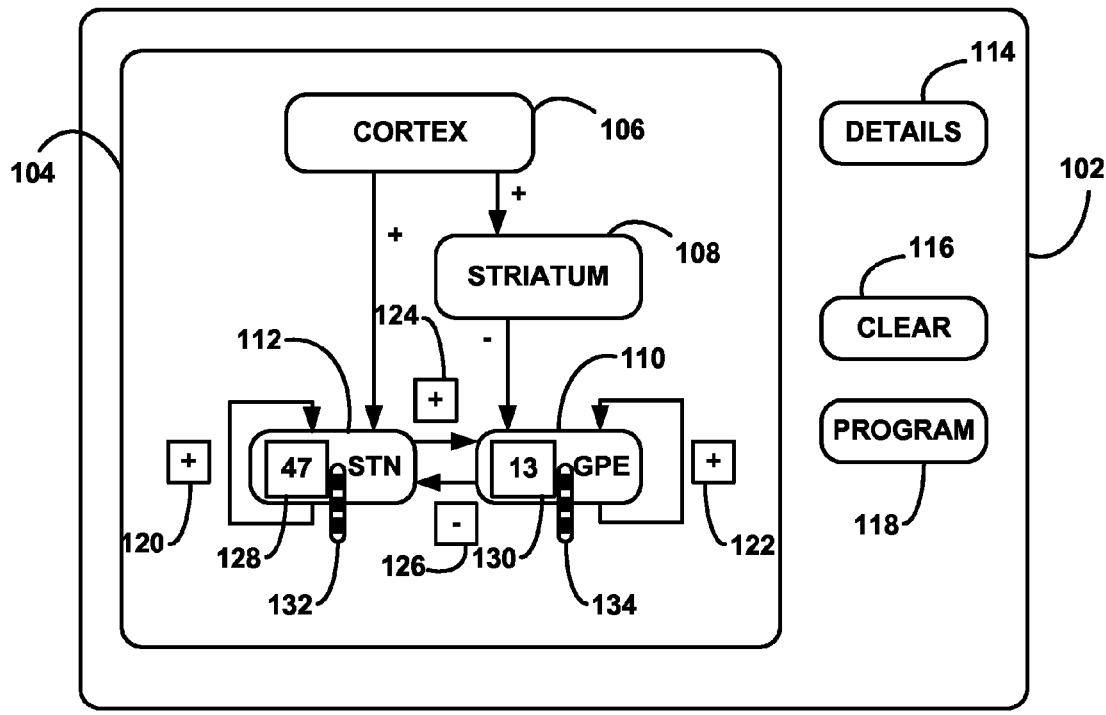
Figure 4C:
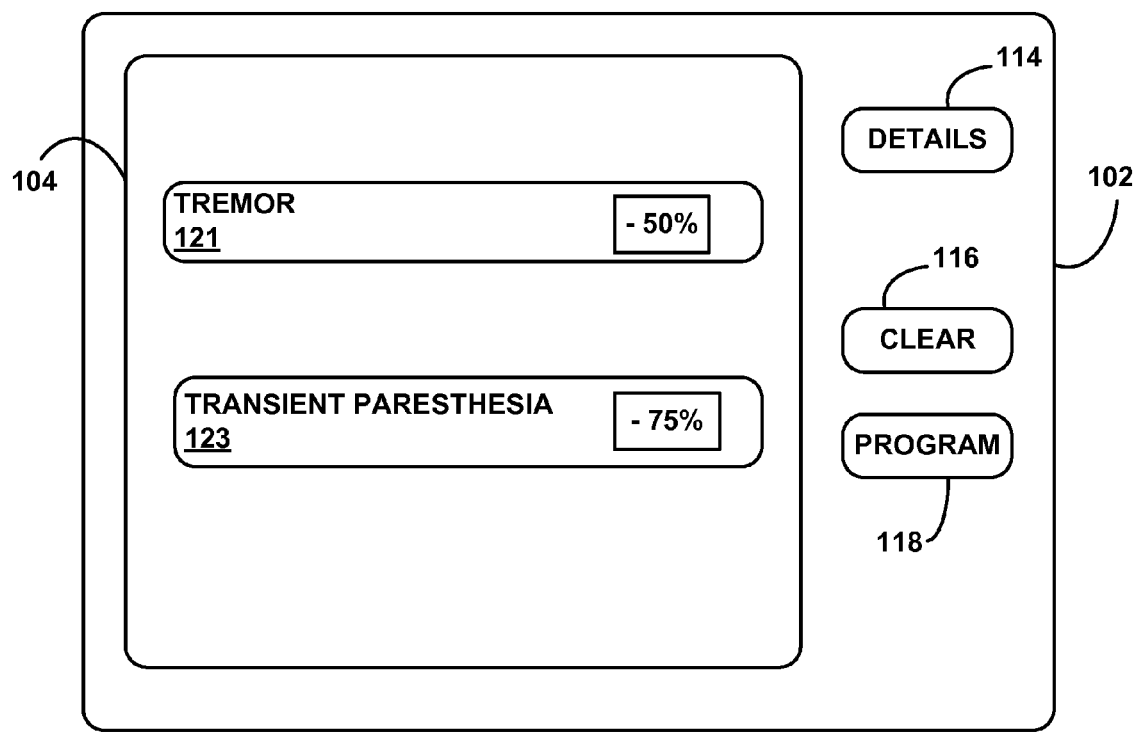

FIGS. 4A-4C illustrate an example programmer graphical user interface (GUI) 102, which processor 53 may present to a user via a display of user interface 59 of programmer 40. As described above with respect to FIG. 3, in some examples, programmer 40 may be a clinician programmer 20 (FIG. 1), while in other examples, programmer 40 may be a patient programmer 22. FIGS. 4A-4C illustrate an example user interface for programming stimulation therapy for of patient 6 receiving stimulation therapy for a particular condition, such as, Parkinson's disease, as an illustrative example. The example model of FIG. 4B illustrates inhibitory and/or excitatory relationships and/or effects between the represented brain structures. In other examples, models of brain networks associated with other diseases or conditions may illustrate other relationships and/or effects among the brain structures. In one example, a model of a brain network may indicate synchronization/desynchronization relationships between brain structures in epileptic syndromes, patterns of activation of brain structures (e.g., as indicated by a time domain or frequency domain characteristic of a bioelectrical brain signal or a signal indicative of hemodynamic activity within the brain) in response to a stimulus such as an acute or chronic pain state. In addition, in other examples, a model of a brain network may include anatomical structures of brain 16 that are relevant to psychiatric disorders, such as major depressive disorder (MDD), obsessive compulsive disorder (OCD), post traumatic stress disorder, an anxiety disorder, and the like. Other types of models that illustrate brain networks associated with other types of patient conditions are contemplated.

In some examples, for a particular patient condition, a clinician may determine the structures of brain 16 that define a brain network by, for example, utilizing a functional magnetic resonance image (fMRI) that indicates neural activity (e.g., based on cerebral blood flow) in brain 16 for particular patient conditions or specific patient states associated with the patient condition. The clinician may deliver stimulation to one structure of brain 16 (e.g., using a probe with an electrode) and determine, based on the fMRI, what other structures of brain 16 are affected by the stimulation. This process may be repeated for any number of structures of brain 16. The group structures that are determined to be interrelated by at least one common anatomical structure, and affected by stimulation delivered to at least one other anatomical structure in the group of structures may then define a brain network.

As FIG. 4A illustrates, programmer 40 may present to the user, via GUI 102, a list of conditions associated with the patient. In another example, GUI 102 may display a general list of conditions that may not all be applicable to patient 6, and a user may select a condition or conditions specific to the patient from the general list. In one example, processor 53 of programmer 40 may retrieve the list of conditions from IMD 34, from memory 55 of programmer 40, from a remote database, or any other storage device associated with programmer 40 or with which programmer 40 can communicate. If the list of patient conditions and, if applicable, associated models of brain networks are stored in another device, processor 53 may retrieve the list of conditions using telemetry module 67 or by connecting directly to a database of patient data. In examples in which processor 53 retrieves the list of conditions from a device other than programmer 40, processor 53 may store the retrieved information in memory 55. In addition to the list of conditions, processor 53 may retrieve or generate a model of brain network associated with each of the conditions. The model of a brain network for a patient condition may be retrieved when the condition is selected by a user by interacting with GUI 102.

Models of brain networks may be unique to a specific patient condition or may cover a variety of related conditions. In one example, models of brain networks may be created based on research (e.g., using the fMRI technique described above) or known literature and stored as libraries in memory 55 of programmer 40. In another example, such libraries may be stored at a central repository accessible by programmer 40, and processor 53 of programmer 40 may retrieve libraries relevant to a patient condition from the central repository at time of use/programming. In some examples, the stored libraries may be periodically updated based on the latest research or the latest clinician knowledge, such that at the time of retrieval by programmer 40, the latest library for a given patient condition is available. In other examples, processor 53 of programmer 40 or another device may generate or configure models of brain networks from a default model at time of implant or at the time of first programming based on physiological sensing and patient-specific factors determined/generated by clinical procedures, e.g., using the fMRI technique described above.

In the example of FIG. 4A, GUI 102 may list brain networks for a plurality of patient conditions, such as Parkinson's disease 105, dystonia 107, and epilepsy 109, which may be associated with patient 6 or may be a general list of conditions not patient-specific. The user may select a condition for which the user wishes to configure a stimulation therapy program by interacting with GUI 102, e.g., clicking on the respective condition. Upon receiving the user input, processor 53 of programmer 40 may present to the user GUI 102 via a display of user interface 59 (FIG. 3), a model of a brain network associated with the selected patient condition. A brain network associated with a selected condition may include structures that are relevant to the condition, and links between the structures indicating the relationship between the structures, where the relationship may be an indication of the effect of one structure on another one or more structures. Abnormalities in brain function associated with a patient condition may result in generating abnormal electrical activity or abnormal hemodynamic activity in certain structures of brain 16. These structures may be used to generate a model of a brain network that illustrates the functional relationship among the brain structures of the brain network. The structures of the brain network may be structures where activity indicative of the presence or severity of a condition is observed, or structures that affect functions of other structures outside the brain network where activity is observed.

The model of the brain network includes structures of brain 16 that are affected by or that affect characteristics (e.g., symptoms) of the patient condition. For example, a decrease in power in a given frequency band (e.g., beta) may result in a decrease in a symptom state (e.g., tremor in Parkinson's disease). Processor 53 of programmer 40 may receive user input via the user interface 59 indicating a desired therapeutic outcome of a therapy delivered to patient 6 by stimulator 34. Processor 53 generates a stimulation therapy program based on user input, by translating user input into stimulation parameter values that the IMD applies to produce the desired therapeutic outcome. In some examples, such as when programmer 40 is used for more than one patient or upon initial set-up of patient-dedicated programmer 40, a user may set up a profile for patient 6 and a programming session for patient 6 prior to selecting a therapy program with the aid of GUI 102.

Programmer 40 may provide the user with options and selections via GUI 102 that allow the user to select the implant location of one or more leads 12 or the intended implant location of the leads if the leads have not been implanted yet. The implant location can be, for example, the structures in brain 16 in which leads 12 are located or structures that an electrical field resulting from stimulation therapy may cover. In one example, the options and selections may include location (e.g., as indicated by stereotactic coordinates or another coordinate system) of the tip of a lead or its individual electrodes; location of at least one of the tip of a lead or an electrode with orientation information (e.g., angles of leads or electrodes relative to a known coordinate system) such that other coordinates can be determined; options with which the user can directly specify location of the one or more leads on a post surgical image; model numbers or physical dimensions of a given lead; a set of measured physiological signals associated with electrodes from which location information can be inferred (e.g., the location of a lead can be determined based on biomarkers); or other information relevant to establishing the location of lead elements relative to brain structures.

In one example, the lead implant location information may be stored in IMD 4 or may be available from a previous programming session and stored in memory 55 of programmer 40. In one example, processor 53 may retrieve lead implant information and automatically place lead icons 132 and 134 on the brain structures in which they are implanted, based on lead location information available to programmer 40 or in IMD 4. In one example, programmer 40 may allow the user to access the lead implant location information. In other examples, the user may provide input specifying the lead implant location.

As FIG. 4B illustrates, programmer GUI 102 includes display screen 104, and selection buttons 114, 116, and 118. Display screen 104 may present to the user options from which to select and go from one screen to another. The user may use selection buttons 114, 116, and 118 to make selections or otherwise provide input, and/or soft keys that GUI 102 may present to the user on display screen 104. In addition or in other examples, the user may interact with a touch screen to make selections and provide other types of input.

Lead implant information may be, for example, coordinates (e.g., stereotactic coordinates or another three-dimensional coordinate system) relative to a known frame of reference for one or more lead elements (e.g., tip, electrode centers, or the like). In other examples, lead implant information may be, for example, a coordinate in addition to a set of angles that may be used to determine other coordinates associated with the electrodes of the lead. In addition to or instead of coordinates, lead implant information may also be, for example, associations between lead elements (e.g., tip, electrodes, or the like) and anatomical structure boundaries within the brain. For example, lead implant information may specify that a first electrode is wholly within a patient's left STN, a second electrode is partially within left STN, a third electrode is outside left STN, and the like.

In some examples, programmer 40 may be configured to receive image-driven information entry, such that the user may specify lead implant location by placing lead graphics on an image of the brain presented by GUI 102 or by registering lead elements to the image via a series of user inputs (e.g., selecting lead elements by touching or clicking with a user input device each electrode on a lead image). In one example, a subset of lead elements may be used to identify lead implant location (e.g., a first and last electrode) where processor 53 of programmer 40 may determine locations of other electrodes of the lead using known dimensions and spacing of electrodes to interpolate locations of electrodes based on identified locations of a subset of electrodes, for example. In this example, the user may be able to drag a lead graphic to structures of the brain where the lead is implanted, rotate and apply curves to the lead graphic.

As part of the set up of GUI 102, processor 53 may allow the user to calibrate the therapy system to obtain baseline information for the leads 12 and for structures of brain 16 affected by the stimulation therapy (e.g., structures covered by an electrical field generated by the delivery of stimulation by stimulation generator 34 via leads 12). During calibration and baseline-obtaining, processor 53 of programmer 40 may determine, given placement of leads relative to one or more anatomical structures of brain 16 and/or each other if multiple leads are implanted within patient 6, the relationship between the effect on the behavior of structures in the brain network and changes in therapy parameter values. For example, processor 53 may determine a relationship between values of therapy parameters and the activity of the structure. For example, processor 53 may determine an electrode combination, and parameter values associated with the electrode combination (e.g., pulse width, pulse amplitude, and the like) that may cause an increase in the activity of a brain structure when stimulation is applied to the brain structure using the determined electrode combination and stimulation parameter values. In one example, the relationship between the stimulation parameter values and a brain structure may be determined by processor 53 (e.g., by controlling stimulator 34 to deliver stimulation according to the selected parameter values and then sensing activity within the brain structure during or immediately following the delivery of stimulation). In another example, the relationship between stimulation parameter values and a brain structure may be known and stored, e.g., in memory 55.

In one example, the behavior of the brain structures may be expressed in terms of the amount of inhibition or activation of one or more other brain structures. In one example, calibration may involve sensing and/or stimulating using each electrode to measure and/or elicit a response, then associate the response to an appropriate structure in the model brain network. For example, sensing a particular frequency band at one electrode may imply that the electrode is in a specific anatomical structure. In another example, stimulating an electrode to elicit a given response may imply correlation of that electrode with a specific anatomical structure known to produce that response.

When the user completes setting up a current programmer session, GUI 102 may display on display screen 104 a model of the brain network associated with the specified leads and patient condition. The brain network model may include graphical representations of brain structures corresponding to structures of the brain network, where the graphical representation of the brain structures may be images of the brain structures or schematic representations of the brain structures. In one example, the graphical representations of the brain structures may be positioned to represent their actual positions relative to one another in the brain, or may be positioned so that structures are placed near structures to which they are linked in the model. The brain structures of the brain network may not be the entire brain structure, but a region of a brain structure that makes up less than the entire brain structure. In one example, the user can interact with the structures of the brain network model by changing inhibitory or excitatory effects of the structures of the brain network. The model of the brain network may resemble a network with elements representing brain structures affected or associated with a selected patient condition. In one example, within the displayed model of the brain network, the brain structure may be graphically represented by network components, which are functionally connected with one another, and may have inhibitory and/or excitatory effects on other brain structures, as illustrated. When anatomical structures of brain 16 are functionally connected, a change in one anatomical structure may affect one or more structures to which it connects. In one example, the effect may be a sensed brain behavior or activity.

The example of FIG. 4B is an example model of a brain network for brain therapy associated with Parkinson's tremor. In this example, the model may comprise cortex 106, striatum 108, subthalamic nucleus (STN) 112, and globus pallidus (GPe) 110. The graphical links, e.g., lines, between these structures may indicate the relationship between structures. The relationship may be, for example, the effect of stimulation in one structure on the activity in one or more other structures. For example, in the example shown in FIG. 4B, the "+" may indicate an excitatory effect, and the "−" may indicate an inhibitory effect. For some structures of the brain network displayed by GUI 102, there may be a feedback effect on the structure itself, e.g., a stimulation of a structure may cause an inhibitory or excitatory effect on the structure itself.

In the example of FIG. 4B, GUI 102 includes lead icons 132 and 134 representing electrodes implanted in STN 112 and GPe 110. Lead icons 132 and 134 may be schematic depictions of leads 12 and respective electrodes 11 or may be images of leads 12 and respective electrodes 11 (FIG. 1). The electrodes, their configuration, and the parameter values associated with stimulation the electrodes deliver to brain 16, may impact the response of the structures, STN 112 and GPe 110, which may impact (e.g., alleviate or increase the severity) symptoms of Parkinson's disease, such as tremor. In one example, the implanted electrodes may deliver electrical stimulation with certain stimulation parameter values to one or more portions of the brain network shown in FIG. 4B, which may cause the associated structure, e.g., the structure to which stimulation is delivered, to increase its excitatory effect on other structures. For example, a certain stimulation parameter values associated with the electrodes implanted in STN 112, may have a certain excitatory effect on GPe 110. Other configurations of the same electrodes may cause an increase in a structure's inhibitory effect.

In the example of FIG. 4B, the excitatory/inhibitory effects between the brain structures are primarily bioelectrical activity (e.g., stimulation of one structure results in increasing/decreasing neural activity in a linked structure based on the relationship between them, i.e., excitatory/inhibitory, respectively). In this example, stimulation of STN 112 may cause the electrical (or neural) activity in GPe 110 to increase.

The GUI 102 may present the model of the brain network, and indicate an existing relationship between the anatomical structures of the brain network at an initial set of stimulation parameter values, and whether the user can change an effect of a certain structure on another or itself. For example, connection between cortex 106 and striatum 108 and other structures in this model show the effect on the other structures by the "+" and "−" indications. However, processor 53 of programmer 40 can configure GUI 102 such that the "+" and "−" indications may not be highlighted by selectable buttons, and, therefore, the user may not be able to directly change the effect cortex 106 and striatum 108 impose on other structures of the brain network shown in FIG. 4B.

As the user manipulates the intensity of stimulation applied to structures in the brain network, such as STN 112 and GPe 110, the effects on cortex 106 and striatum 108 may change accordingly. The intensity of stimulation can be a function of, for example, the electrodes used to deliver stimulation to brain 16, the current or voltage amplitude of the stimulation signal, and other stimulation signal parameters (e.g., frequency or, in the case of pulses, pulse width). In some examples, processor 53 can provide indications of the effect structures have on other structures of the network or on themselves, e.g., by presenting values within GUI 102 that reflect the magnitude of the impact of the structures on each other or on itself. The value of the magnitude of the impact may be a unitless number, but may provide the user with an indication of the effect structures have on one another. For example, in the example shown in FIG. 4B, the magnitude of impact on STN 112 is displayed as a unitless value 128. Similarly, in the example shown in FIG. 4B, the magnitude of the impact of stimulation on GPe 110 may be displayed as a unitless value 130.

In one example, the magnitudes of impact may represent a measure of the sensed activity in the associated structure. In one example, the magnitudes of impact may be generated by comparing a sensed value of a physiological parameter with a baseline value. The baseline value may be, for example, measured during or soon after implant of leads 12 in brain 16 and stored in memory 55 of programmer 22 or memory 52 of IMD 34, a value measured in the absence of a stimulation state, or may be a theoretical value established by research or literature and simply used as reference. The magnitude of impact may be expressed as a ratio (e.g., sensed value/baseline value), as a percentage change (e.g., increase or decrease relative to the baseline value), or as a magnitude of change from the baseline value (e.g., an absolute value of the increase or decrease). In one example, the sensed activity may be a measure of a function of the structure that is associated with the patient condition or certain symptoms of the condition. The function may refer, for example, to an electrical function of the structure (e.g., energy in a spectral band of a bioelectrical brain signal sensed in the structure, an action potential rate associated with the structure, and the like) that is known to correlate with a clinical outcome (e.g., symptom, side effect, and the like). In the example of FIG. 4B, for Parkinson's disease, the function of STN 112 may be a measure of energy in the beta band of a bioelectrical brain signal sensed within STN 112, which may indicate the presence and/or the severity of tremor in a patient with Parkinson's disease. For example, it is believed that abnormal activity within a beta band (e.g., about 8 hertz (Hz) to about 30 Hz or about 16 Hz to about 30 Hz) of a bioelectrical brain signal is indicative of brain activity associated with a movement disorder (e.g., Parkinson's disease). In other examples, the function may refer to an amount of blood flow out of or into a structure that is known to correlate with a clinical outcome.

In some examples, the connections between anatomical structures of a brain network may be configured such that stimulation delivered to one anatomical structure can result in more or less synchronized activity (e.g., electrical activity or hemodynamic activity) with another structure of the brain network, more or less power in a given spectral band (e.g., amount of energy present in a frequency band between specified lower and upper frequency bounds as extracted using a Fourier transform) relative to another brain structure or relative to a baseline, or other controllable effects of interest in the circuit. The measure of the sensed activity may be obtained by, for example, sensing bioelectrical brain signals with electrodes 48 of stimulator 34 in a unipolar or bipolar configuration, or determining hemodynamic activity (e.g., blood pressure or blood flow or volume) with leads 12 which can include a pressure sensor or a pulse oximeter. Sensing module 58 (FIG. 2) of stimulator 34 or another sensing module may be used to sense the physiological parameter and processor 53 may determine the sensed activity based on a signal generated by sensing module 58.

Referring to FIG. 4B, the user may interact with GUI 102 to adjust and manipulate the effects of stimulation applied to certain brain structure in the illustrated model network. In the example shown in FIG. 4B, the user may adjust the effects of each of STN 112 and GPe 110 on one another by selecting buttons 124 and 126, where the "+" button 124 may indicate an excitatory effect and the "−" button 126 may indicate an inhibitory effect. For example, a user input that increases an excitatory effect to a given structure may cause a change in the sensed level of activity (e.g., bioelectrical brain signal amplitude or power level within one or more frequency bands or hemodynamic activity) in that structure. Processor 53 of programmer 40 may determine the therapy parameter values that would result in the change to the excitation of the brain structure indicated by the user.

Processor 53 may then apply the determined therapy parameter values and measure the sensed activity in the structures indicated by the user. If the sensed level of activity does not change as expected based on the user input, the system may indicate to the user that there is a mismatch. In one example, if a mismatch is indicated, processor 53 may attempt the requested change (e.g., the increased excitatory effect to the structure) using a different set of parameters than the parameters initially used. In other examples, if the sensed level does not change as expected based on user input, the system may propose adjustments to the network model (e.g., make links stronger or weaker, change links from excitatory to inhibitory, or change the location of a lead relative to structures to more accurately reflect changes made to stimulation). In one example, the system may adjust the strength of the links by making a link stronger or weaker. The strength of a link between structures may indicate a gain associated with the link between the structures, which can be used to predict activity in one structure based on activity in another structure with which it links. In the example of FIG. 4B, stimulation of STN 112 increases the activity in GPe 110, and the amount of increase depends, among other factors, on the strength of the link between STN 112 and GPe 110. In one example, if the sensed level of activity in GPe 110 does not change as expected based on user input, the system may propose adjusting the strength of the link between STN 112 and GPe 110 by making it stronger, for example. Making the link stronger may increase the gain associated with the link, and as a result, stimulation of STN 112 at the same level as previously attempted, may result in a higher level of sensed activity in GPe 110.

In the example shown in FIG. 4B, the user may also adjust the effects of each of STN 112 on itself and GPe 110 on itself using the buttons 120 and 122, respectively. In one example, the effects of stimulation delivered to the brain network shown in FIG. 4B on each of STN 112 and GPe 110 may be represented using a value, instead of or in addition to "+" and "−" signs, where increasing or decreasing the effect is displayed as a number, e.g., percentage of a maximum value. STN 112 and GPe 110 may each be associated with implanted electrodes as illustrated, which may provide an indication of sensed activity in these structures. In one example, the sensed activity may be a bioelectrical brain signal, e.g., EEG, ECoG, a local field potential (LFP) reflecting activity of a population of neurons, a single neuron's spike train via a microelectrode, or the like. The sensed activity may be indicated using a value, as shown in the boxes with numbers inside each of the structures, where the value reflects the magnitude of the impact of the structures on each other or on itself, and may be expressed using a unitless number. In other examples, the value representing the sensed activity may be a direct measure of the power in a band of interest, e.g., beta, gamma, alpha, etc., or degree of synchronicity of the bioelectrical brain signal associated with the structure, time domain characteristics of a bioelectrical brain signal (e.g., a mean, median, peak or lowest amplitude, instantaneous amplitude, pulse frequency or pulse to pulse variability), frequency domain characteristics of a bioelectrical brain signal (e.g., an energy level in one or more frequency bands), or some other measurable characteristic of a sensed physiological signal, which may be sensed within brain 16

As the user interacts with the network displayed in GUI 102 and adjusts the stimulation effects by, for example, selecting the icons with "+" and "−" signs, processor 53 dynamically adjusts the stimulation parameters based on the user input. For example, processor 53 may adjust the stimulation parameters to values that help achieve the desired stimulation effects. The effect of therapy delivered by stimulator 24 that the user indicates by interacting with GUI 102 may change the activity (e.g., electrical brain signal activity or hemodynamic activity) sensed in each of the affected structures. The user may determine based on the changes in the sensed activity whether the adjustments are resulting in the desired effect. For example, the sensed activity may be a measure of the power in a band of interest, and a decrease in sensed activity (e.g., power in a beta frequency band of a sensed bioelectrical brain signal) may be known to correlate to a decrease in a symptom state (e.g., tremor).

As the user adjusts the effects of stimulation therapy on structures of brain 16, processor 53 can adjust the parameter values (e.g., electrode combinations and configurations, stimulation signal amplitude, stimulation signal frequency, and the like) accordingly. Processor 53 may use a mapping algorithm to determine the stimulation parameter values, e.g., lead configuration, pulse width and rate, amplitude, etc., that will yield the outcome or effect specified by the user. In one example, processor 53, when implementing the mapping algorithm, may control stimulation generator 60 of stimulator 34 (FIG. 2) to apply stimulation to each electrode 48 in sequence. Processor 53 may then obtain objective measures of outcome, e.g., beneficial therapeutic effects or stimulation-induced side effects at various stimulation amplitudes. The objective measures of outcome from the stimulation delivery can be determined, e.g., based on a physiological parameter (e.g., a bioelectrical brain signal or a hemodynamic parameter) sensed by a sensing module of stimulator 34 or another sensing module that may be physically separate from stimulator 34.

Processor 53, when implementing the mapping algorithm (which can be stored as instructions executable by processor 53), may store the obtained measures of the outcome of stimulation delivery and subsequently use them to propose new stimulation settings given desired outcomes by reverse association and/or interpolation. In some examples, the mapping between the high level network effects, e.g., user adjustments to effects between structures of a brain network may be performed using heuristics or guidelines associated with the network. For example, prior testing by a clinician or computer modeling can indicate that certain frequencies of stimulation may have a given effect on certain structures, and after the user specifies a desired therapeutic outcome, the adjusted effect is mapped to a corresponding frequency. In either example, the user may adjust the effects of the structures and the stimulation therapy, without having to directly configure any stimulation parameters at a lower level.

Mapping of stimulation parameter values to particular effects of therapy delivered stimulator 34 may be configured as to provide an efficient combination of therapy parameter values that yield the desired effect. For example, processor 53 may propose settings that achieve a given desired outcome in a specific order (e.g., least energy consuming settings to most energy consuming settings) for trial with patient 6. In this example, the least energy consuming settings may correspond to stimulation with lower intensity (e.g., lower frequencies, smaller pulse widths, lower amplitudes, and/or fewer active electrodes). While multiple therapy programs may help achieve a user-indicated effect of therapy, processor 53 may select the therapy program that provides the most efficient usage of power.

In one example, the user may wish to see how adjusting effects of structures, e.g., stimulating one structure to generate a desired sensed activity in another structure in the network influences the configuration of the stimulation parameters (e.g., the stimulation parameter values). GUI 102 may provide the user with button 114, the selection of which may present a user interface that presents details of the medical device programming at a lower level, e.g., visualization of tissue effects (e.g., volume of tissue activated, an electrical field that represents structures of brain 16 that will be covered by an electrical field generated by the delivery of electrical stimulation, or a voltage gradient or a current density model that indicates the voltage gradient or current density of the electrical field) or stimulation settings and parameter values. In one example, GUI 102 may provide a split screen option for the user to see both the higher level model network interactive screen 104, and the stimulation parameter values. In this example, as the user changes effects between structures in the model network, the user can see the corresponding changes in stimulation parameter values to achieve the desired effect as indicated by the user.

In the examples using the model of brain network, the user may have an understanding of the effect each structure's sensed activity has on the patient condition, e.g., the relationship between the sensed activity in STN and the amount of tremor experienced by a patient. For example, the user may understand how the activity level in STN affects an outcome, e.g., right arm tremor, and/or a side effect, e.g., transient paresthesia. As illustrated in FIG. 4C, in one example, GUI 102 may provide the user with a higher level of visualization and programming, and allow the user to specify a balance between the therapeutic benefits outcome and stimulation-induced side effects. In this example, GUI 102 may display on display screen 104, a list of symptoms and side effects associated with a condition, e.g., tremor 121 and transient paresthesia 123 in the example shown in FIG. 4C. The user may selectively increase or decrease the therapeutic outcomes and side effects. For example, the user may indicate a desired outcome of 50% less tremor and 75% less transient paresthesia. These percentages may be relative to a baseline patient state in no symptoms of the patient condition with which patient 6 is afflicted are present, or a patient state specific to patient 6 in which the patient symptoms were reduced and/or the stimulation-induced side effects were minimized or even eliminated.

Upon receiving user input indicating the desired relative levels of therapeutic benefits outcome and stimulation-induced side effects, processor 53 of programmer 40 may determine adjustments to the stimulation settings based on the brain network associated with the patient condition by increasing or decreasing excitation or inhibition of adjustable structures, e.g., STN 112 and GPe 110, in the example shown in FIG. 4B. In one example, processor 53 may determine adjustments to brain network (e.g., relative levels of excitation or inhibition of the anatomical structures) by using relationships established in a previous mapping of the anatomical structures to outcomes, or by using relationships established by previous research efforts or available in the literature (e.g., knowledge that stimulation of STN decreases tremor). Processor 53 may determine adjustments to the stimulation parameter values based on understandings of the propagation of electrical energy in brain tissue (e.g., knowledge that stimulation of STN decreases tremor, and that to further decrease tremor the STN must be stimulated at a higher amplitude than previously attempted). Processor 53 may also translate the adjustments in the brain network into changes in programming parameter values applied to specific electrodes, as determined and optimized by the mapping algorithm.

In one example, the user may wish to revert to the default settings to restart the programming process, and may select button 116 labeled "clear" to return to the default setting before the user started making any changes. In one example, the default settings may be the stimulation parameter values from the most recent programming session. In another example, the default settings may be the stimulation parameter values believed to be effective for some patients with the same condition as the patient. Once the user finishes making changes and adjustments, the user may select button 118 labeled "program" to program stimulator 34 using the adjusted program settings. Processor 53 of programmer 40 causes the transmission of the adjusted therapy program to stimulator 34 via the respective telemetry modules 67, 56, and processor 50 of stimulator 34 may receive the adjusted therapy program and control stimulation generator 60 to generate and deliver stimulation to patient 6 based on the adjusted therapy program.

Figure 5:
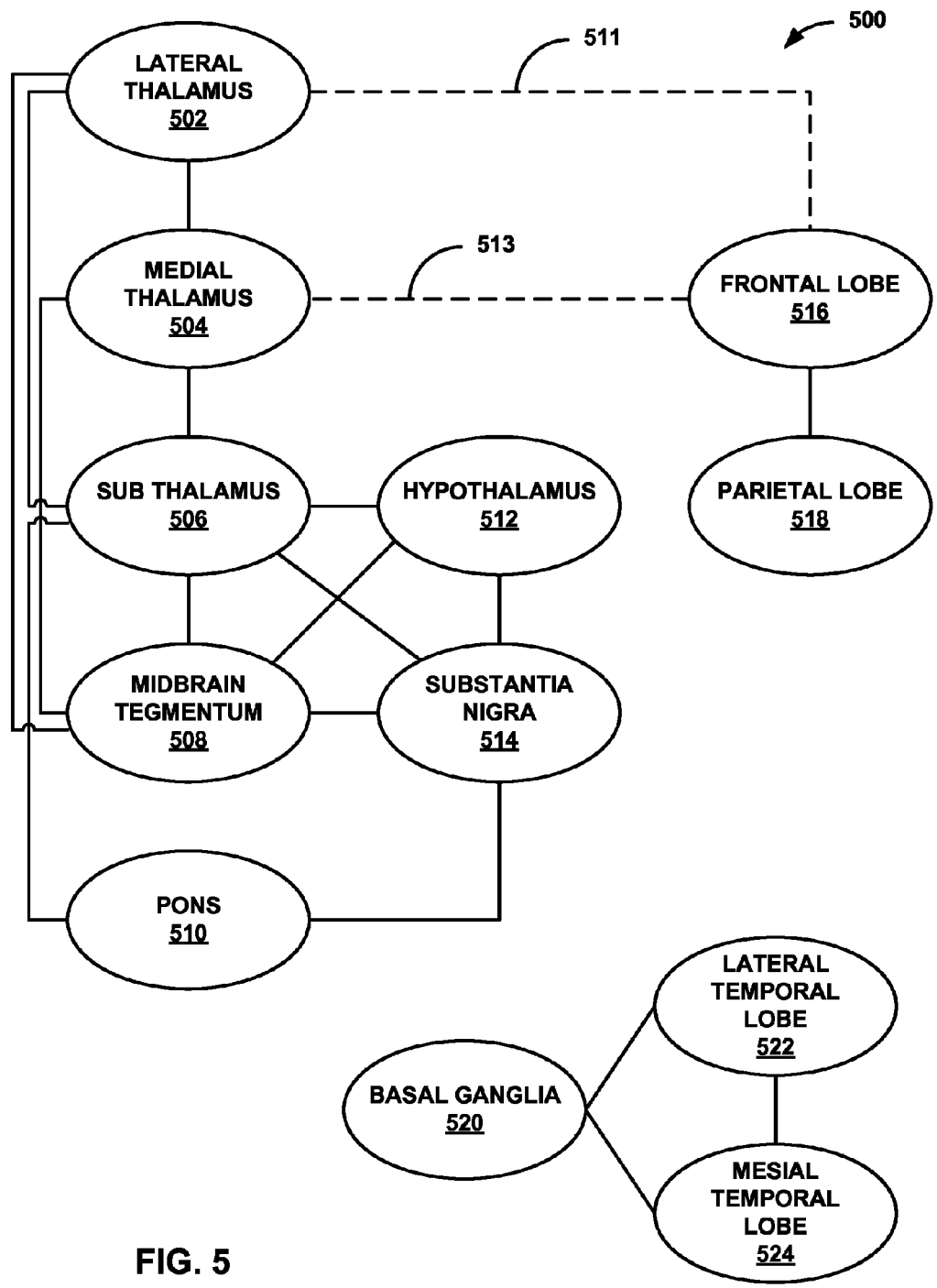
FIG. 5 illustrates an example model of a brain network associated with epilepsy.

As previously described, processor 53 of programmer 40 can control user interface 59 to display a model of a brain network associated with patient conditions other than movement disorders, receive user input via the model indicating a desired effect of therapy, and determine one or more stimulation parameter values based on the user input. In some examples, the brain network includes one or more anatomical structures (or regions of an anatomical structure) that affect or are affected by symptoms of the patient condition. FIG. 5 illustrates an example model 500 of a brain network associated with epilepsy. In the example shown in FIG. 5, model 500 of the brain network associated with epilepsy includes lateral thalamus 502, medial thalamus 504, sub thalamus 506, midbrain tegmentum 508, pons 510, hypothalamus 512, substantia nigra 514, frontal lobe 516, parietal lobe 518, basal ganglia 520, lateral temporal lobe 522, and mesial temporal lobe 524, which are anatomical structures of brain 16 of patient 6 that may be affected or have an effect on a patient with epilepsy. In the example of FIG. 5, the effects between structures may correspond to positive and negative correlations between the structures, where delivery of electrical stimulation that increases cerebral blood flow (CBF) in one structure may increase or decrease CBF in another structure of the network. A positive correlation may be indicated by a solid connection between structures and indicates that an increase/decrease in CBF in one structure causes an increase/decrease in CBF in a connected structure, and a negative correlation may be indicated by a dotted connection (e.g., connections 511 and 513) between structures and indicates that an increase/decrease in CBF in one structure causes a decrease/increase in CBF in a connected structure.

Figure 6:
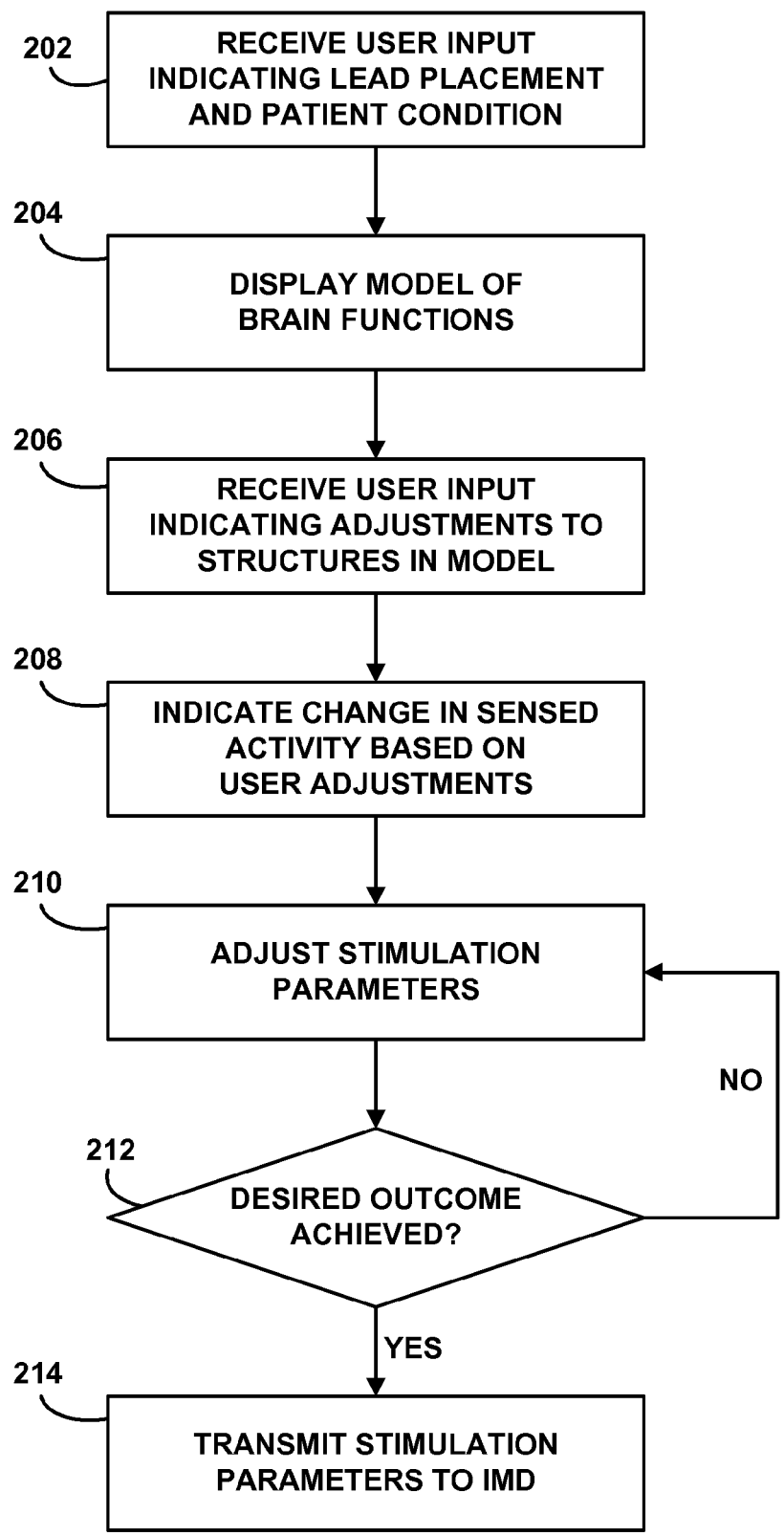
FIG. 6 is a flow diagram of an example technique for programming a medical device.

FIG. 6 is a flow diagram of an example technique for programming a medical device by generating a user interface that presents a model of a brain network, and selecting stimulation parameter values based on user input provided via the user interface. A programmer, e.g., programmer 40, receives user input via user interface 59 to initiate programming of a stimulation program for delivering therapy to a patient, where the user input indicates lead placement and patient condition (202). In some examples, processor 53 may present to the user a list of conditions associated with the patient, and the user may select the condition for which the user wishes to configure the stimulation therapy program.

Thus, in some examples, the user input may indicate the lead placement and the patient condition for which the user is programming the stimulation therapy. In one example, processor 53 may retrieve lead placement information stored in memory 55 (FIG. 2) from a previous session or at time of implant. The lead placement information may include, for example, coordinates in three-dimensional space of electrodes of the leads (e.g., stereotactic coordinates).

As part of the set up of a programming session, programmer 53 may present a user interface via user interface 59 to the user that permits the user calibrate the therapy system to obtain baseline information for the leads implanted in patient 6 and for brain structures affected by the stimulation therapy. In one example, calibrating the system may include stimulating electrodes expected to yield a given therapeutic effect, and then sensing a physiological signal (e.g., a bioelectrical brain signal or a signal indicative of a hemodynamic characteristic) of patient 6 to determine whether the stimulation delivery actually elicited the effect (e.g., inhibition or excitation of electrical activity). The sensed information may be subsequently used to refine the determination of stimulation parameter values given a user-indicated desired effect on a brain structure or outcome (e.g., eliminating or minimizing tremor). During calibration and baseline-obtaining, processor 53 of programmer 40 may determine, given placement of leads, the relationship between the effect on the behavior of structures in the brain network and changes in stimulation parameter values. In one example, the behavior of the structures may be expressed in terms of the amount of inhibition or activation of a certain structure.

Programmer 40 may display, via user interface 59, a model of the brain network associated with the specified leads and conditions (204). In some examples, the brain network model may include graphical representations of anatomical brain structures with which the user may interact by changing applied stimulation that affects the inhibitory or excitatory effects on that brain structure. In other examples, the brain network model may include graphical representations of anatomical rain structures with which the user may interact by changing applied stimulation to change the synchronization or desynchronization of electrical activity within the brain structures.

The model of the brain network may resemble a network with elements representing brain structures affected or associated with a patient condition. The structures may be functionally connected with each other, and the stimulation of one structure may have inhibitory and/or excitatory effects on another structure within the network. In the example shown in FIG. 6, processor 53 of programmer 40 may receive user input via user interface 59 that indicates one or more adjustments to the inhibition or excitation of one or more structures of the brain network displayed by user interface 59 (206). The adjustments may reflect increasing or decreasing the inhibitory and/or excitatory effect of adjustable structures on other structures.

Processor 53 can control user interface 59 to display an indication of the changes in the sensed activity at the structures of the brain network as the user adjusts the effects of the structures (208). In some examples, user interface 59 may indicate the sensed activity using a unitless value. In other examples, the value may be a direct measure of the power in a band of interest of a bioelectrical brain signal, e.g., beta, gamma, alpha, etc., or degree of synchronicity of the signal with another bioelectrical brain signal (e.g., sensed at another part of the brain network), or some other measurable characteristic of the signal. As the user utilizes user interface 59 to interact with the brain network and adjust the effects of the structures, processor 53 may cause the execution of instructions in accordance with the mapping algorithms stored in memory 55 to dynamically adjust the stimulation parameter values to values at which the user-indicated desired effect of therapy may be achieved (210).

In some examples, memory 55 of programmer 40 or a memory of another device (e.g., stimulator 34 or a remote database) may associate an effect of therapy with a therapy parameter value or a change to a therapy parameter value. For example, memory 55 may store a particular excitation level (e.g., as indicated by the unitless value displayed by GUI 102 or by a particular bioelectrical brain signal characteristic or a hemodynamic characteristic) of STN 112 and associate the excitation level with a particular stimulation parameter value (e.g., a frequency value, a current or voltage amplitude, or pulse width if stimulator 34 delivers stimulation signals in the form of pulses) or a therapy program that defines values for each of a plurality of stimulation parameters. As another example, memory 55 may associate a particular percentage of synchronization of bioelectrical brain signal activity in STN 112 and GPe 110 with one stimulation parameter value or a therapy program that defines values for each of a plurality of stimulation parameters. In some examples, processor 53 may adjust the stimulation parameter values to values based on the user input indicating a desired effect of therapy delivery by stimulator 34 by accessing a data structure within memory 55 to determine which one or more stimulation parameter values are associated with the therapeutic effect indicate by the user.

In some examples, processor 53 implements a mapping algorithm, which may be stored in memory 55 (FIG. 3) to perform computations to configure the stimulation parameters, e.g., lead configuration, pulse width and rate, amplitude, etc., that will yield the outcome or effect specified by the user. In some examples, the mapping between the high level network effects, e.g., user adjustments to effects between structures may be performed using heuristics or guidelines associated with the brain network. In some examples, processor 53 may utilize the mapping algorithm to provide an efficient combination of programming parameter values that yield the desired effect. For example, certain frequencies of stimulation may have a given effect on certain structures, and as the user specifies a desired effect of stimulation therapy, the adjusted effect is mapped to a corresponding frequency. In either example, the user may adjust the effects of stimulation on the structures of the brain network and the stimulation therapy without having to directly configure any stimulation parameters at a lower level.

In some examples, stimulator 34 includes a sensing module that is configured to sense a physiological parameter of patient 6, such as a bioelectrical brain signal within brain 16 or a hemodynamic characteristic (e.g., blood pressure, blood volume or blood flow) within brain 16. In other examples, a sensing module separate from stimulator 34 may sense the physiological parameter to determine a sensed activity value in the affected structures. Processor 53 may receive the raw sensed physiological signal waveform, a parameterized signal waveforms, or any other data other than the raw signal waveform, and determine whether the sensed physiological signal indicates the adjustments to the stimulation parameters resulted in the desired therapeutic effect (e.g., outcome) (212). For example, the sensed physiological parameter may be a measure of the power in a band of interest, and a decrease in the sensed physiological parameter (e.g., power in a beta frequency band of a sensed bioelectrical brain signal) may be known to correlate to a decrease in a symptom state (e.g., tremor). Therefore, in the example of Parkinson's disease, if the desired outcome is a decrease in tremor, processor 53 may evaluate the effectiveness of a stimulation based on the amount of decrease of power in the beta frequency band of a bioelectrical brain signal. If the desired therapeutic effect is not achieved, processor 53 may readjust one or more of the stimulation parameter values (210) using values that may result in the desired outcome.

Processor 53 may iteratively repeat the determination whether the desired outcome is achieved (212) and adjustment of the stimulation parameter values (210), until there is an indication that the adjusted parameters achieve the desired outcome. In this manner, the mapping algorithm may adjust the model and parameter value predictions utilizing techniques such as, for example, regression learning, trial and error, analytical approaches (e.g., solving a system of equations), finite element techniques, or the like. In one example, when processor 53 determines or receives an indication that the desired outcome is achieved, processor 53 transmits, using telemetry module 67, the program parameters to IMD 4 (214), which may apply stimulation therapy according to the received program. In other examples, processor 53 may store the program parameters in memory 55 or may transmit the program parameters to a database. The processor may also transmit the program parameters to a remote program or system for trial stimulation. In some examples, processor 53 may store the program parameters as a starting point for future programming for the associated model.

While the techniques of this disclosure are described in the context of brain neural network activity, it should be understood that the techniques of this disclosure are applicable to functions of other anatomical structure and organs in the body. For example, cardiac functions may be monitored using techniques of this disclosure to determine occurrence of events such as, for example, arrhythmias. In one example, functions of the heart may be monitored and may result in a stable oscillatory trajectory, e.g., the plot of the monitored signal resembles an identifiable shape or circle back to the starting point. Trajectory changes may be a move to non-oscillatory state indicating, for example, an increase in frequency, which may indicate occurrence of fibrillation of the heart. Based on this determination, the system may be moved from the non-oscillatory state to the oscillatory state to restore the heart function to a normal state.

The techniques described in this disclosure, including those attributed to programmer 40, IMD 34 or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 50 of IMD 34 and/or processor 53 of programmer 40, any one or more parts of the techniques described herein may be implemented by a processor of one of IMD 34, programmer 40, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples of the disclosure have been described. These and other examples are within the scope of the following claims.

The invention claimed is:

1. A method comprising:
   displaying, on a user interface of a computing device, a graphical representation of a model of a network of interconnected anatomical structures of a patient, wherein the graphical representation of the network includes graphical links indicating functional relationships between the anatomical structures;
   receiving user input via the user interface specifying at least one effect of therapy delivered by an implantable medical device to at least one of the anatomical structures of the patient; and
   determining, with a processor, one or more therapy parameter values with which the implantable medical device generates therapy based on the user input and the functional relationships between the anatomical structures.

2. The method of claim 1, wherein determining the one or more therapy parameter values comprises:
   determining a relationship between one or more therapy parameters and at least one of the anatomical structures; and
   determining the one or more therapy parameter values based on the relationship between the one or more therapy parameters and the anatomical structures.

3. The method of claim 1, wherein determining the one or more therapy parameter values comprises determining one or more therapy parameter values associated with the at least one effect of therapy in a memory of a device.

4. The method of claim 1, further comprising:
   delivering the therapy to the at least one of the anatomical structures;
   sensing a physiological parameter of the patient;
   determining whether the physiological parameter indicates the at least one effect of therapy specified by the user input; and adjusting the one or more therapy parameter values if the physiological parameter does not indicate the at least one effect of therapy specified by the user input.

5. The method of claim 1, wherein the at least one effect indicates at least one of an excitatory effect or an inhibitory effect on at least one of the anatomical structures.

6. The method of claim 1, wherein the at least one effect indicates at least one of a synchronization or desynchronization between at least two of the anatomical structures.

7. The method of claim 1, further comprising displaying one or more outcomes associated with a patient condition, wherein the at least one effect indicates a desired change to the one or more outcomes.

8. The method of claim 7, wherein the one or more outcomes includes at least one of at least one beneficial therapeutic effect and at least one stimulation-induced side effect.

9. The method of claim 1, wherein the implantable medical device includes an electrical stimulator, and the therapy parameter values define the electrical stimulation delivered by the electrical stimulator to at least one of the anatomical structures.

10. The method of claim 1, further comprising:
displaying, on the user interface, one or more patient conditions;
receiving user input, via the user interface, selecting a patient condition from the one or more patient conditions; and
selecting the graphical representation of the network of interconnected anatomical structures based on the selected patient condition.

11. The method of claim 1, further comprising transmitting the one or more determined therapy parameter values to the implantable medical device.

12. A system comprising:
a user interface that displays a graphical representation of a model of a network of interconnected anatomical structures of a patient, wherein the graphical representation of the network includes graphical links indicating functional relationships between the anatomical structures, wherein the user interface is configured to receive user input specifying at least one effect of therapy delivered by an implantable medical device to at least one of the anatomical structures of the patient; and
a processor that determines one or more therapy parameter values with which the implantable medical device generates therapy based on the user input and the functional relationships between the anatomical structures.

13. The system of claim 12, wherein to determine the one or more therapy parameter values, the processor:
determines a relationship between one or more therapy parameters and at least one of the anatomical structures; and
determines the one or more therapy parameter values based on the relationship between the one or more therapy parameters and the anatomical structures.

14. The system of claim 12, wherein to determine the one or more therapy parameter values, the processor determines one or more therapy parameter values associated with the at least one effect of therapy in a memory of a device.

15. The system of claim 12, further comprising:
a stimulation generator configured to deliver the therapy to the at least one of the anatomical structures; and
a sensor configured to sense a physiological parameter of the patient,
wherein the processor determines whether the physiological parameter indicates the at least one effect of therapy specified by the user input,
wherein the processor adjusts the one or more therapy parameter values if the physiological parameter does not indicate the at least one effect of therapy specified by the user input.

16. The system of claim 12, wherein the user interface displays one or more outcomes associated with a patient condition, wherein the at least one effect indicates a desired change to the one or more outcomes.

17. The system of claim 16, wherein the one or more outcomes includes at least one of at least one beneficial therapeutic effect and at least one stimulation-induced side effect.

18. The system of claim 12, wherein the user interface:
displays, on the user interface, one or more patient conditions;
receives user input, via the user interface, selecting a patient condition from the one or more patient conditions; and
selects the graphical representation of the network of interconnected anatomical structures based on the selected patient condition.

19. The system of claim 12, further comprising a telemetry device that is configured to transmit the one or more determined therapy parameter values to the implantable medical device.

20. The system of claim 12, further comprising a programmer for the implantable medical device, wherein the programmer comprises the user interface and the processor.

21. A system comprising:
means for displaying a graphical representation of a model of a network of interconnected anatomical structures of a patient, wherein the graphical representation of the network includes graphical links indicating functional relationships between the anatomical structures;
means for receiving user input specifying at least one effect of therapy delivered by an implantable medical device to at least one of the anatomical structures of the patient; and
means for determining one or more therapy parameter values with which the implantable medical device generates therapy based on the user input and the functional relationships between the anatomical structures.

22. The system of claim 21, wherein the means for determining the one or more therapy parameter values comprises:
means for determining a relationship between one or more therapy parameters and at least one of the anatomical structures; and
means for determining the one or more therapy parameter values based on the relationship between the one or more therapy parameters and the anatomical structures.

23. The system of claim 21, wherein the means for determining the one or more therapy parameter values comprises means for determining one or more therapy parameter values associated with the at least one effect of therapy in a memory of a device.

24. The system of claim 21, further comprising:
means for delivering the therapy to the at least one of the anatomical structures;
means for sensing a physiological parameter of the patient;
means for determining whether the physiological parameter indicates the at least one effect of therapy specified by the user input; and
means for adjusting the one or more therapy parameter values if the physiological parameter does not indicate the at least one effect of therapy specified by the user input.

25. The system of claim 21, further comprising means for displaying an indication of a function of the at least one of the structures in response to the user input.

26. The system of claim 21, further comprising means for displaying one or more outcomes associated with a patient condition, wherein the at least one effect indicates a desired change to the one or more outcomes.

27. The system of claim 21, further comprising:
means for displaying one or more patient conditions;
means for receiving user input selecting a patient condition from the one or more patient conditions; and
means for selecting the graphical representation of the network of interconnected anatomical structures based on the selected patient condition.

28. An article of manufacture comprising a non-transitory computer-readable medium comprising instructions that, upon execution, cause a processor to:
display, on a user interface of a computing device, a graphical representation of a model of a network of interconnected anatomical structures of a patient, wherein the graphical representation of the network includes graphical links indicating functional relationships between the anatomical structures;
receive user input via the user interface specifying at least one effect of therapy delivered by an implantable medical device to at least one of the anatomical structures of the patient; and
determine one or more therapy parameter values with which the implantable medical device generates therapy based on the user input and the functional relationships between the anatomical structures.

29. The computer-readable medium of claim 28, wherein the instructions to determine the one or more therapy parameter values comprise instructions to:
determine a relationship between one or more therapy parameters and at least one of the anatomical structures; and
determine the one or more therapy parameter values based on the relationship between the one or more therapy parameters and the anatomical structures.

30. The computer-readable medium of claim 28, wherein the instructions to determine the one or more parameter values comprises instructions to determine a therapy parameter value associated with the at least one effect of therapy in a memory of a device.

31. The computer-readable medium of claim 28, further comprising instructions to:
deliver the therapy to the at least one of the anatomical structures;
sense a physiological parameter of the patient;
determine whether the physiological parameter indicates the at least one effect of therapy specified by the user input; and
adjust the one or more therapy parameter values if the physiological parameter does not indicate the at least one effect of therapy specified by the user input.

32. The computer-readable medium of claim 28, further comprising instruction to display, via the user interface, an indication of a function of the at least one of the structures in response to the user input.

33. The computer-readable medium of claim 28, further comprising instructions to display one or more outcomes associated with a patient condition, wherein the at least one effect indicates a desired change to the one or more outcomes.

34. The computer-readable medium of claim 28, further comprising instructions to:
display, on the user interface, one or more patient conditions;
receive user input, via the user interface, selecting a patient condition from the one or more patient conditions; and
select the graphical representation of the network of interconnected anatomical structures based on the selected patient condition.

* * * * *